US011235105B2

(12) United States Patent
Nikon

(10) Patent No.: US 11,235,105 B2
(45) Date of Patent: Feb. 1, 2022

(54) AUTO-INJECTOR

(71) Applicant: Alexander Nikon, Arlington Heights, IL (US)

(72) Inventor: Alexander Nikon, Arlington Heights, IL (US)

(\*) Notice: Subject to any disclaimer, the term of this patent is extended or adjusted under 35 U.S.C. 154(b) by 135 days.

(21) Appl. No.: 16/825,025

(22) Filed: Mar. 20, 2020

(65) Prior Publication Data

US 2021/0290847 A1 Sep. 23, 2021

(51) Int. Cl.
   *A61M 5/20* (2006.01)
   *A61M 5/32* (2006.01)
   *A61M 5/315* (2006.01)

(52) U.S. Cl.
   CPC ...... *A61M 5/2033* (2013.01); *A61M 5/31513* (2013.01); *A61M 5/3202* (2013.01); *A61M 5/3232* (2013.01); *A61M 2005/202* (2013.01); *A61M 2005/2073* (2013.01); *A61M 2005/2086* (2013.01)

(58) Field of Classification Search
   CPC .............. A61M 5/2033; A61M 5/3232; A61M 5/3202; A61M 5/31513; A61M 2005/2086; A61M 2005/202; A61M 2005/2073; A61M 5/3271; A61M 2005/2013; A61M 2005/208
   See application file for complete search history.

(56) References Cited

U.S. PATENT DOCUMENTS

| 7,112,187 | B2 | 9/2006 | Karlsson |
| 8,414,533 | B2 | 4/2013 | Alexandersson |
| 8,992,476 | B2 | 3/2015 | Shang et al. |
| 8,992,477 | B2 | 3/2015 | Raday |
| 9,233,215 | B2 | 1/2016 | Hourmand |
| 9,408,973 | B2 * | 8/2016 | Shang ................. A61M 5/2033 |
| 9,427,525 | B2 | 8/2016 | Barrow-Williams |
| 9,427,531 | B2 | 8/2016 | Hourmand |
| 9,579,464 | B2 | 2/2017 | Cowe |

FOREIGN PATENT DOCUMENTS

| CA | 2862880 A1 * | 8/2013 | ........ A61M 5/31511 |
| WO | WO-2019192971 A1 * | 10/2019 | .......... A61M 5/2033 |

\* cited by examiner

*Primary Examiner* — Theodore J Stigell
*Assistant Examiner* — Rachel T. Smith

(57) ABSTRACT

The auto-injector consists of a front unit connected to a rear unit, wherein the front unit contains a syringe holder with a syringe coaxially sliding between injecting and secure positions within an activating element preloaded via an ejection spring to secure a trigger button through a stopper located in the rear unit.

The rear unit contains a syringe pusher with a plunger managed via a controller coaxially moved by an injection spring to the front unit upon activating the trigger for injecting medication. After the injection, the activating elements revert to allow the controller to release the syringe which moves into to secure position with the syringe holder and the plunger by the ejection spring.

When the syringe enters a safe position, the controller moves by the injection spring between the activating element and the syringe holder to prevent the syringe from sliding toward the injection side.

12 Claims, 30 Drawing Sheets

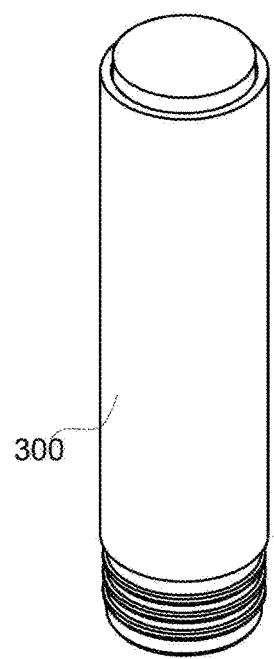
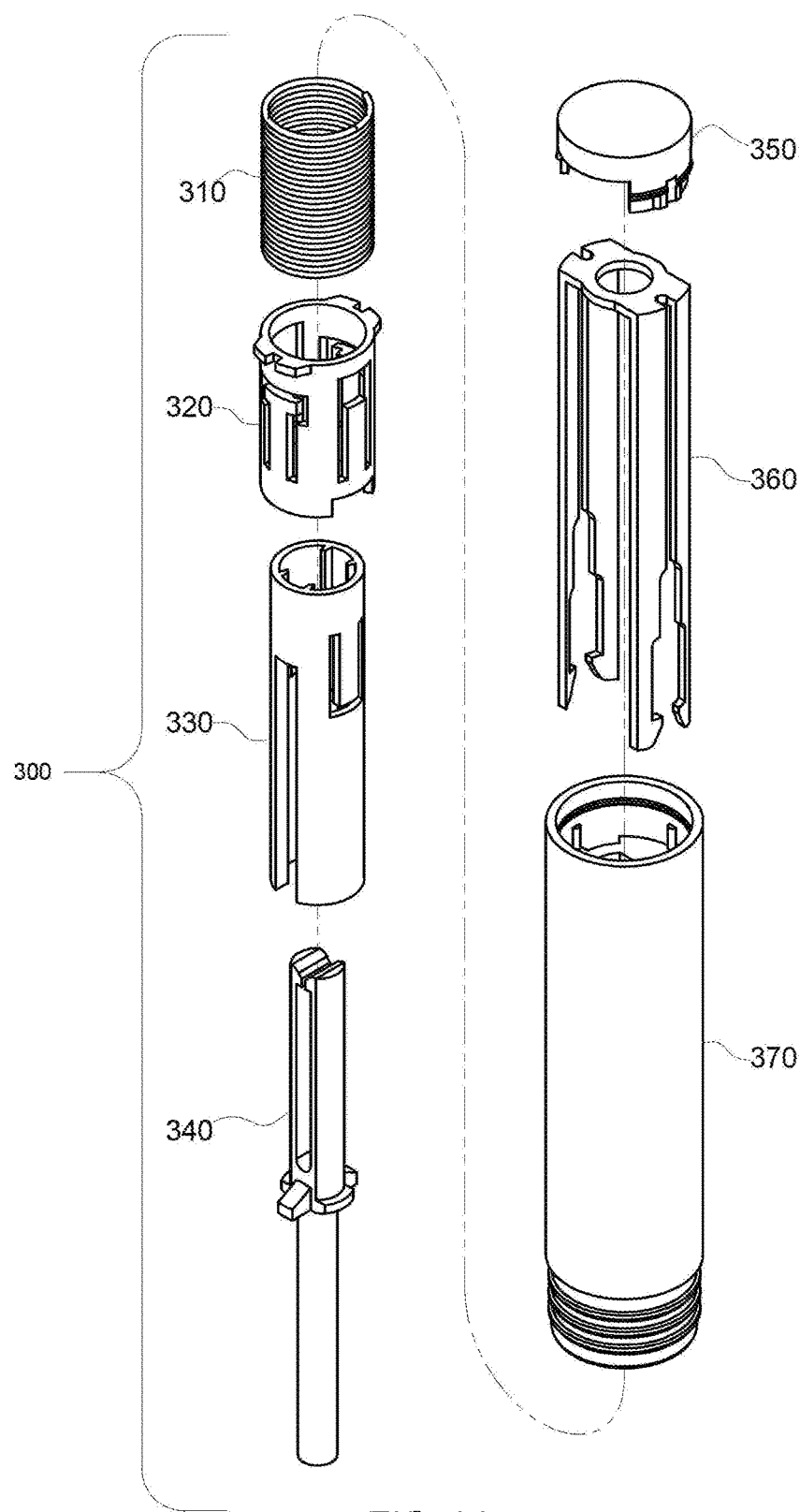
FIG. 9
FIG. 9A

FIG. 22A   FIF. 22B

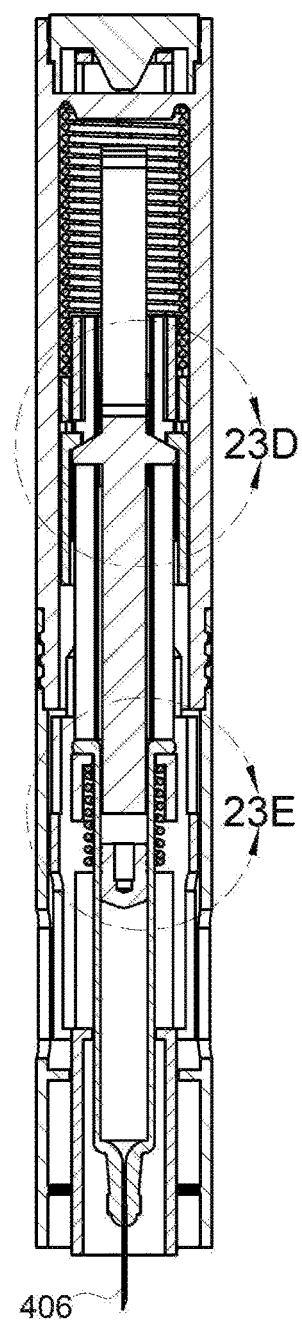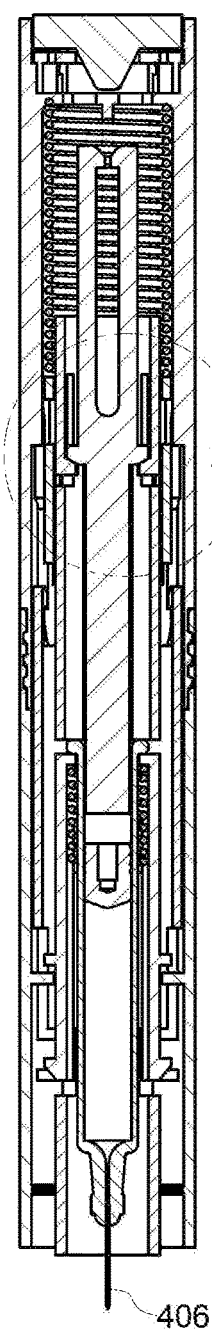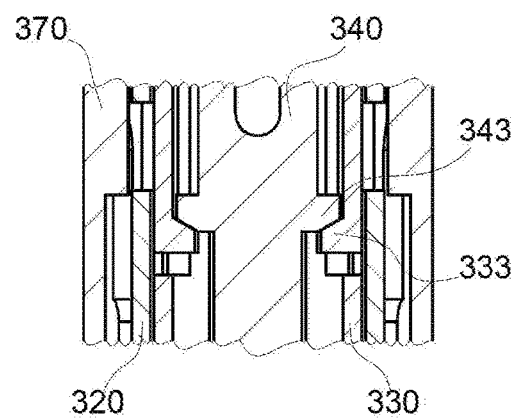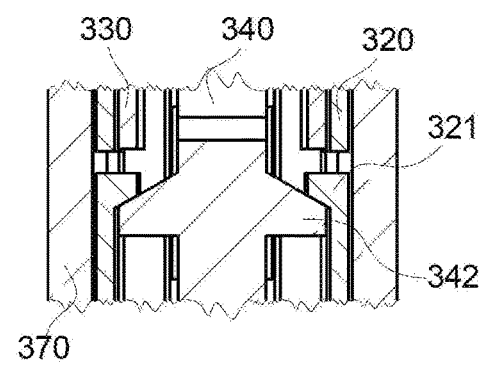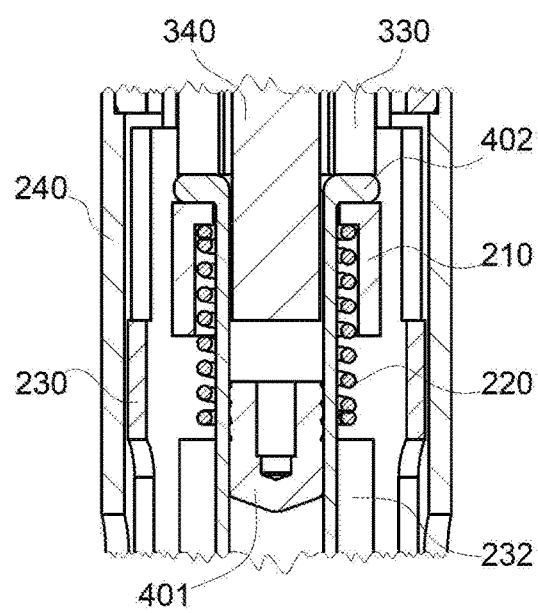
FIG. 23A
FIG. 23B
FIG. 23C
FIG. 23D
FIG. 23E

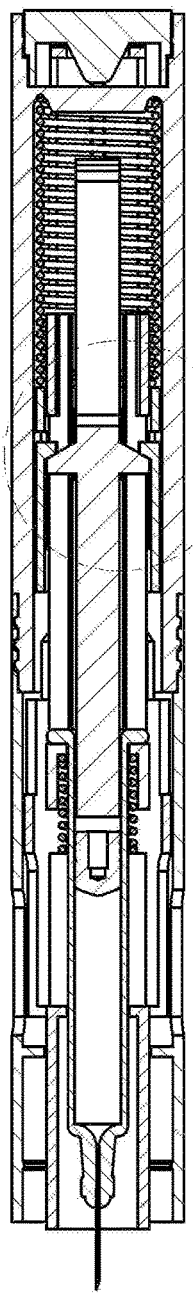
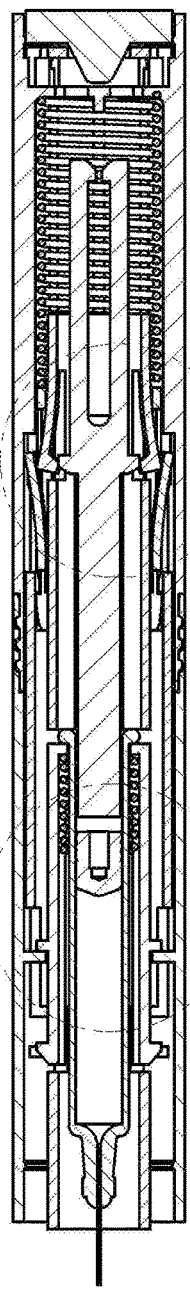
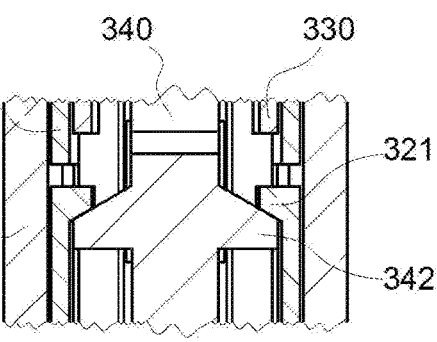
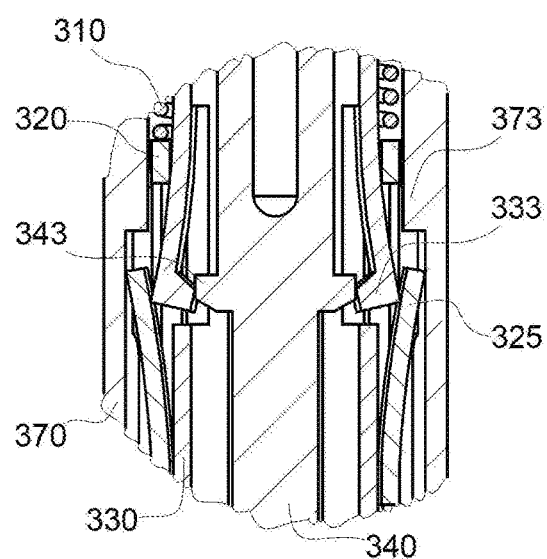
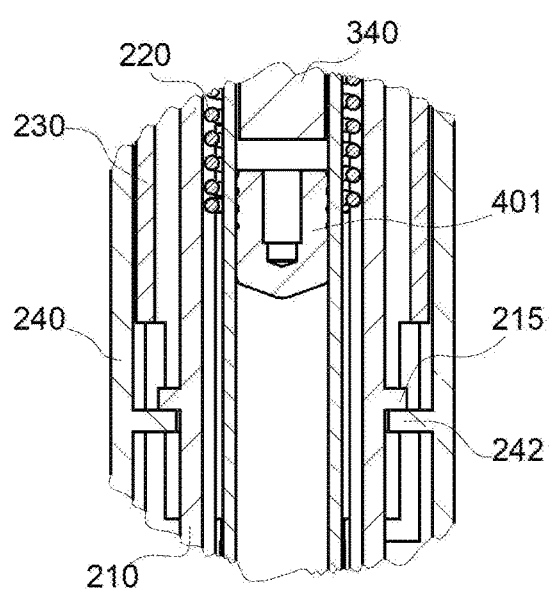
FIG. 24A   FIG. 24B
FIG. 24C
FIG. 24D
FIG. 24E

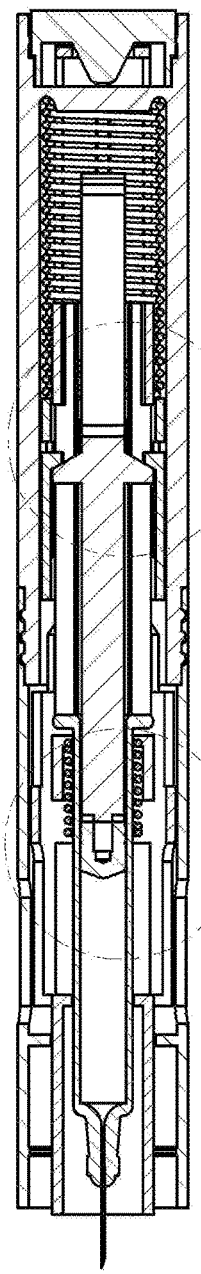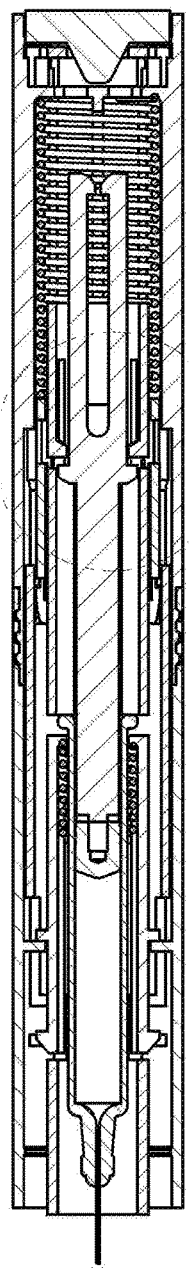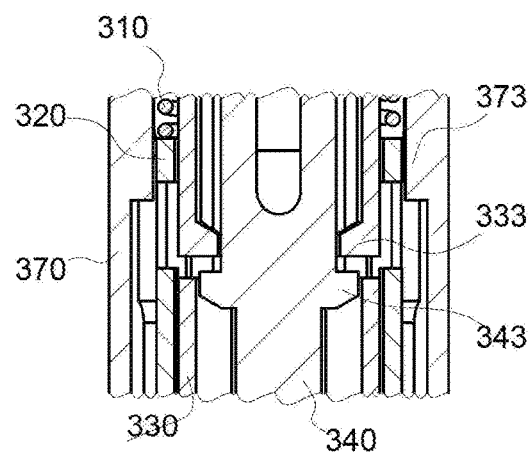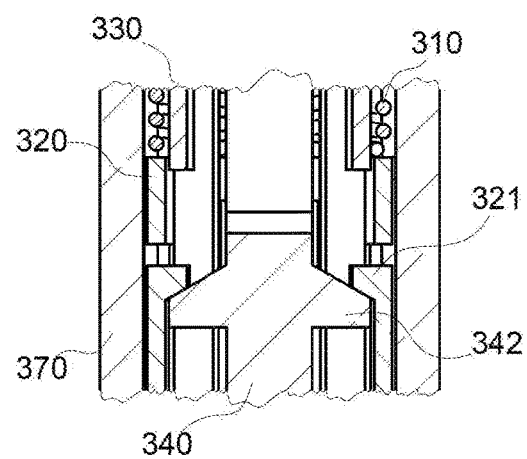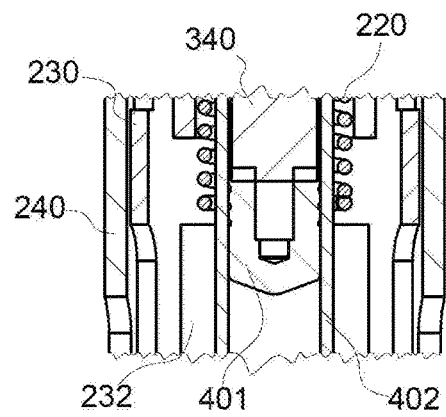
FIG. 25A
FIG. 25B
FIG. 25C
FIG. 25D
FIG. 25E

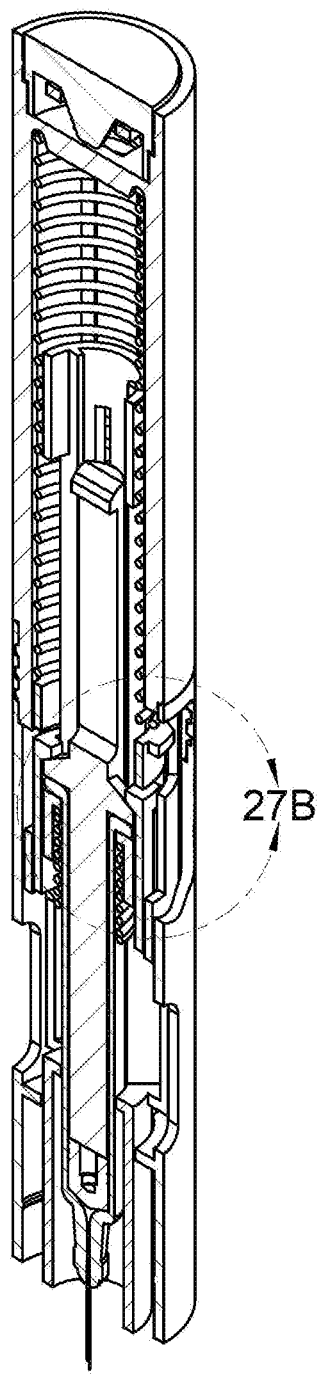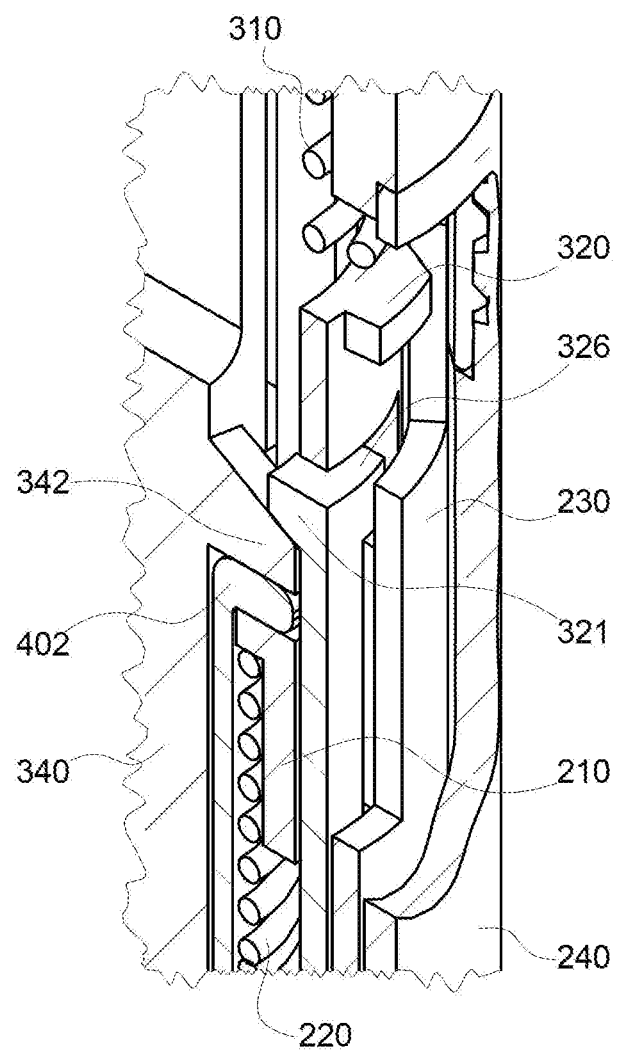
FIG. 27A
FIG. 27B

AUTO-INJECTOR

CROSS-REFERENCE TO RELATED APPLICATIONS

| | | | |
|---|---|---|---|
| 7,112,187 B2 | Sep. 26, 2006 | Anders Karlsson | 604/187 |
| 8,414,533 B2 | Apr. 9, 2013 | Oscar Alexandersson | 604/131 |
| 8,992,477 B2 | Mar. 31, 2015 | Lior Raday | 604/136 |
| 9,233,215 B2 | Jan. 12, 2016 | Yannick Hourmand | 604/134 |
| 9,408,973 B2 | Aug. 9, 2016 | AbbVie Inc. | 604/131 |
| 9,427,525 B2 | Aug. 30, 2016 | Timothy Barrow-Williams | 604/134 |
| 9,427,531 B2 | Aug. 30, 2016 | Yannick Hourmand | 604/134 |
| 9,579,464 B2 | Feb. 28, 2017 | Toby Cowe | 604/136 |

FEDERALLY SPONSORED RESEARCH

Not Applicable

SEQUENCE LISTING OR PROGRAM

Not Applicable

BACKGROUND

Field of Invention

This invention relates to medical devices for delivering the medicine, specifically to an auto-injection apparatus for bringing media into the body in a subcutaneous, intramuscular way.

Prior Art

Nowadays in the market exist so many different types the auto-injector devices for self-administering injection, capable of delivering medications from the prefilled container with the needle to patients under emergency condition, such as to administer epinephrine to counteract the effects of a severe allergic reaction.

Moreover, some patients, however, can be averse to carrying out self-injection, particularly if the petitioner has a fear of the needles or limited dexterity.

Furthermore, the auto-injector should further be provided with safety to prevent accidental needle sticks from used needles due to the contamination hazards.

Therefore, the auto-injectors are alternative devices to a syringe for delivering a therapeutic agent.

In general, all auto-injectors are capable to deliver the dose of medication, but not all devices have the protection from improper use.

The U.S. Pat. No. 8,992,476 describes the auto-injector comprise an additional cap to cover an activation button thus prevent accidental activation of the activation button during final assembly or transportation. After, remove the cap the patient has the ability for accidental activation the device and spills the medication.

Also, the injection device has a stepped shroud with two flexible arms for covering the needle of the syringe upon the injection was performed. Those flexible arms prevent the stepped shroud to slide back into a device as long as they do not get enough load to bend again and free the stepped shroud.

Moreover, the plunger has a compressible expanded central portion, named as the plunger elbows to move the syringe toward to injection side, and stick the needle of the syringe into patient's skin. This type of piston does not prevent the spill of the drug in case if one elbow of the plunger lost its stiffness or the mechanism has higher friction between parts.

However, a medical delivery device described above with all the presented flaws exist and there is still a possibility for improvements to make a current device more robust and secured.

SUMMARY OF THE INVENTION

The aim of the present invention is to remedy the drawbacks of the auto-injection device for injecting a substance, such as a therapeutic agent, into a patient. The purpose and advantages of the disclosed subject matter will be set and pointed out in the claims, as well as from the appended drawings.

According to the invention, the auto-injector consists of two main units: front unit and rear unit.

The front unit consists of a front housing containing the activator with the syringe holder which encloses the ejection spring keeping the activator protruded from the injection side of the front housing and the syringe holder both being arranged along a longitudinal axis under the influence the ejection spring. Furthermore, the front unit has a cover located on the injection end of the front unit to protect the activator.

The rear unit consists of the rear housing with the injection spring compressed via the controller withheld by the plunger arranged along a longitudinal axis into a locked position under the influence of the stopper.

The stopper is not able to release the plunger because it is secured via the trigger button which prevents the accidental activation during transportation or assembly with the front unit. Moreover, the controller interacts with the syringe pusher which manages the movement of the syringe into the injection position upon activation of the auto-injector.

Finally, assemble the front and rear units together by installing the syringe, to exclude access to the syringe and protect the syringe from the damage. After the assembly, the activator and the stopper unite and have a coaxial motion, as one piece.

It is necessary to release the stopper in order to activate the auto-injector via the trigger button. For that, the trigger button must be rotated to a certain degree in order to free the stopper. When the assembly is done the auto-injector is ready to be packaged for delivery to the patient.

When the patient needs to administer medication, they should remove the cover of the auto-injector in conjunction with the shield which seals the needle of the syringe and provides access to the protruded activator located on the injection side of the device.

The trigger button may only be activated if the activator is pressed against the skin of the patient thereby shifting the activator with the stopper inside to release the plunger.

When the trigger button is pressed, the injection spring displaces the controller which in turn guides the plunger with the syringe pusher to the syringe, whereby the needle of the syringe penetrates the patient's skin. Only after that, the controller frees the syringe pusher and forwards the plunger to perform the administration of the drug into the body, thereby preventing the spill of the drug.

When the injection is completed, the patient withdraws the auto-injector from their skin, whereby the activator slides back protruded position by the ejection spring and permits the controller to slide forward. This allows the syringe holder with the syringe and the plunger to return back into the device by the ejection spring to a secure position.

Whereupon the controller slides between the activator and the syringe holder by the injection spring and prevent the syringe from sliding back to the injection position.

These and other aspects of and advantages with the present invention will become apparent from the following detailed description of embodiments of the invention and from the accompanying drawings.

BRIEF DESCRIPTION OF THE DRAWINGS

The present invention will become more fully understood from the detailed description given herein below and the accompanying drawings which are given by way of illustration only, and thus, are not limited of the present invention, and wherein:

FIG. 9 is an isometric view of the rear unit assembly 300 of the auto-injector 100.

FIG. 9A is an exploded isometric view of the rear unit assembly 300.

FIG. 22A is the cross-section view of the auto-injector 100 taken along the section line A-A on the FIG. 18A.

FIG. 22B is the cross-section view of the auto-injector 100 taken along the section line B-B on the FIG. 18B.

FIG. 23A is the cross-section view of the auto-injector 100 taken along the line A-A on the FIG. 18A.

FIG. 23B is the cross-section view of the auto-injector 100 taken along the section line B-B on the FIG. 18B.

FIG. 23C is the detailed view of the auto-injector 100 taken from the FIG. 23B.

FIG. 23D is the detailed view of the auto-injector 100 taken from the FIG. 23A.

FIG. 23E is the detailed view of the auto-injector 100 taken from the FIG. 23A.

FIG. 24A is the cross-section view of the auto-injector 100 taken along the section line A-A on the FIG. 18A FIG. 24B is the cross-section view of the auto-injector 100 taken along the section line B-B on the FIG. 18B.

FIG. 24C is the detailed view of the auto-injector 100 taken from the FIG. 24A.

FIG. 24D is the detailed view of the auto-injector 100 taken from the FIG. 24B.

FIG. 24E is the detailed view of the auto-injector 100 taken from the FIG. 24B.

FIG. 25A is the cross-section view of the auto-injector 100 taken along the section line A-A on the FIG. 18A.

FIG. 25B is the cross-section view of the auto-injector 100 taken along the section line B-B on the FIG. 18B.

FIG. 25C is the detailed view of the auto-injector 100 taken from the FIG. 25B.

FIG. 25D is the detailed view of the auto-injector 100 taken from the FIG. 25A.

FIG. 25E is the detailed view of the auto-injector 100 taken from the FIG. 25A.

FIG. 27A is an isometric view of the FIG. 26A with the break out view to show the hidden portion of the part.

FIG. 27B is the detailed view of the auto-injector 100 taken from the FIG. 27A.

DETAILED DESCRIPTION OF THE INVENTION

The embodiment of the auto-injector according to the invention shown in FIG. 1 and described below is designed to inject a selected dose of the medication when placed upon the injection zone and applied.

Figure 1:
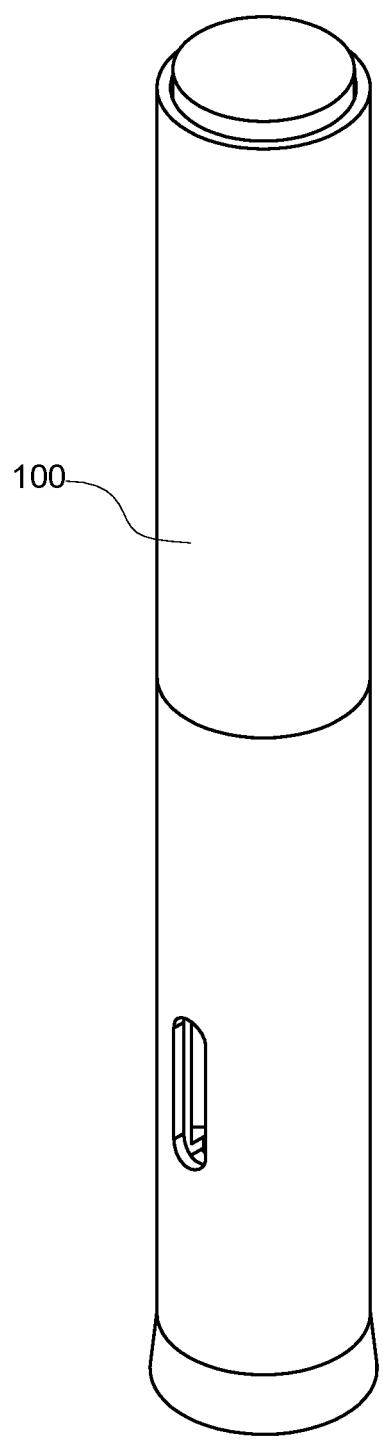
FIG. 1 is an isometric view of the auto-injector 100 according to an illustrative embodiment of the disclosed subject matter.

Referring initially to FIG. 1 the auto-injector 100 comprises of the front unit 200 and rear unit 300 assembled in the final stage of assembly in order to defend the syringe assembly 400 with a dose of medication inside the auto-injector.

Figure 2:
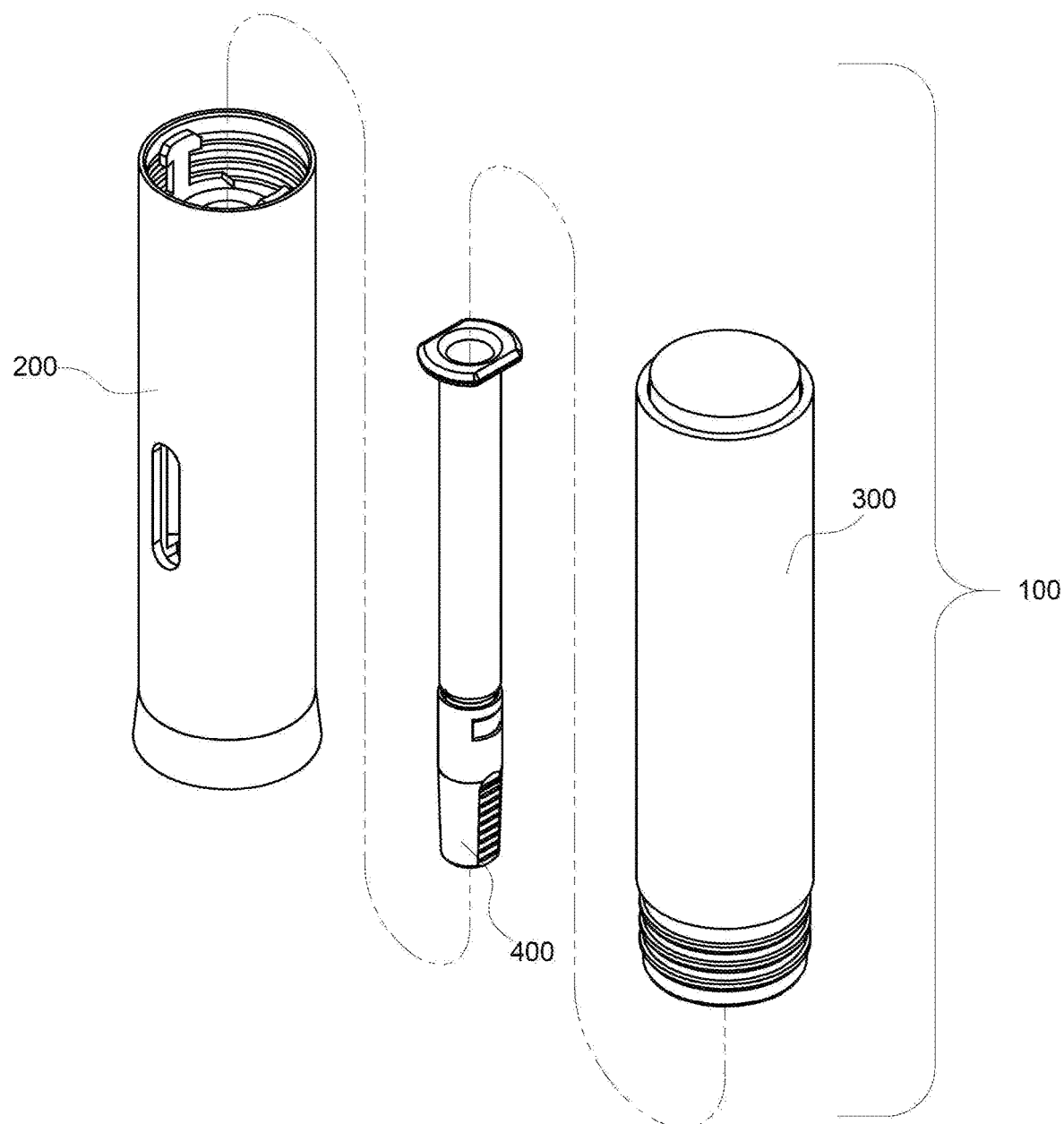
FIG. 2 is an exploded view of the auto-injector 100 which consists of the front unit 200, the rear unit 300 and the syringe assembly 400.

For a better understanding look to FIG. 2 which illustrates the simplified exploded view of the auto-injector 100 assembly.

Figure 3:
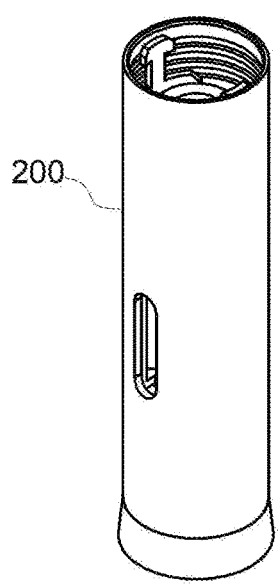
FIG. 3 is an isometric view of the front unit assembly 200 of the auto-injector 100.
Figure 3A:
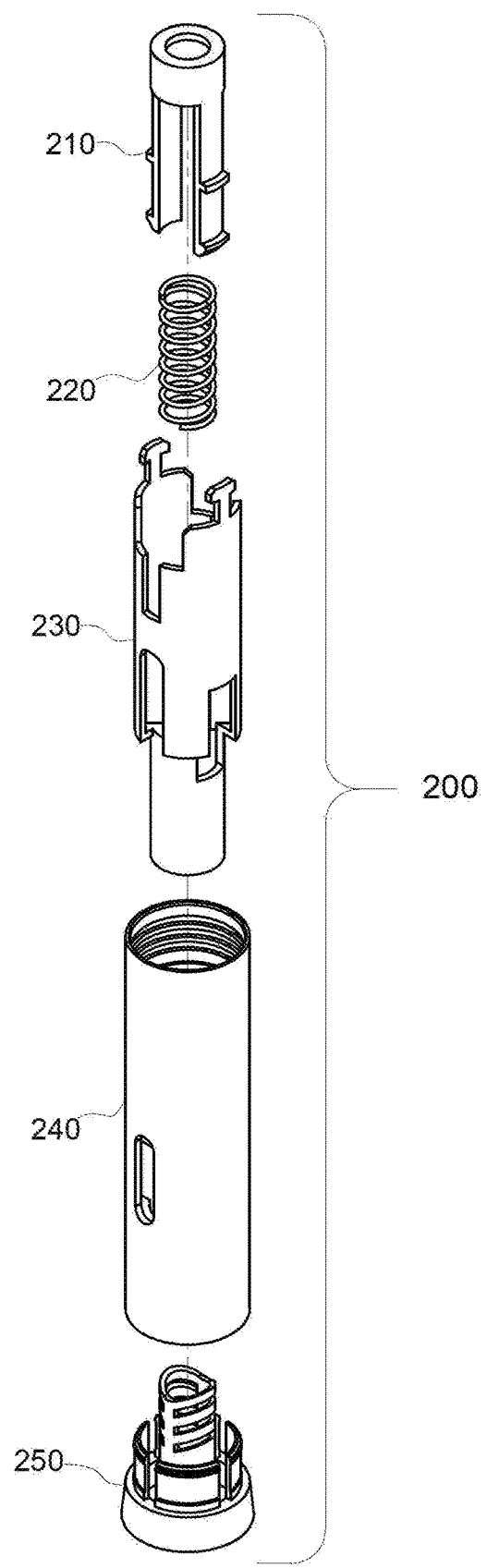
FIG. 3A is an exploded isometric view of the front unit assembly 200.

The front unit assembly 200 illustrated in FIGS. 3 and 3A, is the respective isometric pre-assembled view and the simplified exploded view accordingly.

The front unit assembly 200 consists of the following components like the front housing 240, the activator 230 which positioned coaxially to the front housing with the ejection spring 220 and the syringe holder 210 from the one side respectively to the front housing 240 and the cap 250 from another side.

Figure 4:
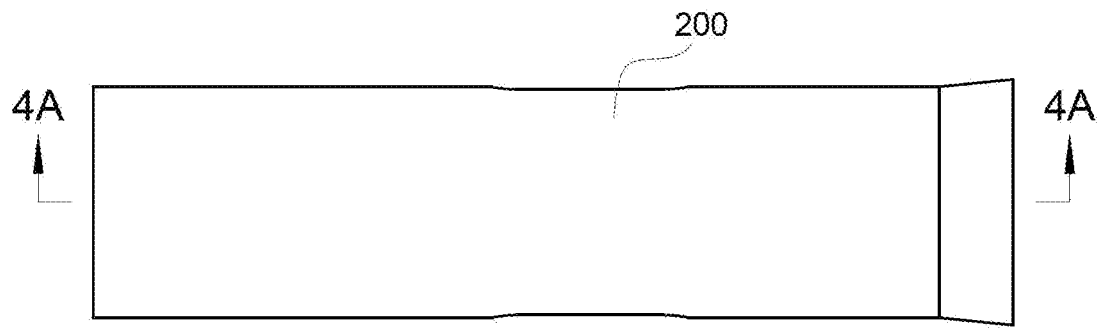
FIG. 4 is the side view of the front unit 200 to present the section line 4A-4A.
Figure 4A:
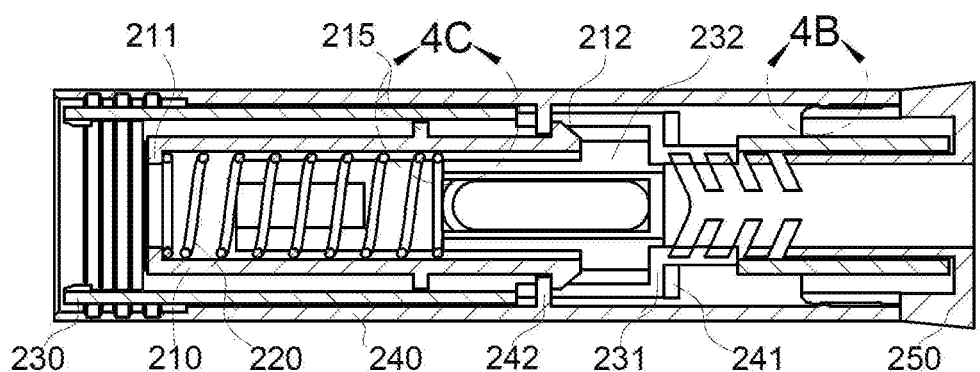
FIG. 4A is the cross-section view of the front unit 200 taken along the section line 4A-4A of the FIG. 4.

Referring to the FIGS. 4 and 4A which illustrates the assembled front unit 200 with the section line 4A-4A and side section view respectively for a better representation of the interaction and the location of the details among themselves.

Initially, the activator 230 is coaxially inserted into the front housing 240 until stopped by stops 231 of the activator 230 touches the ribs 241 of the front housing 240 as shown in FIG. 4A. For better clarity of the location of these parts, the ribs 241 of the front housing 240 see the section view of the front housing 240 in FIG. 5B and the stops 231 of the activator 230 presented in FIG. 6.

Figure 4B:
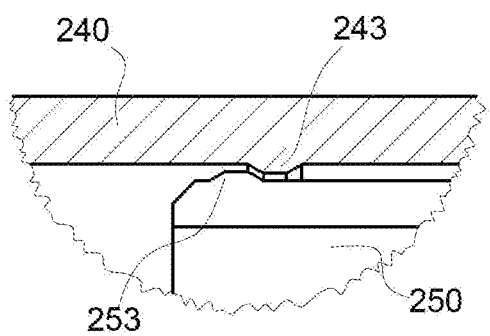
FIG. 4B is the detailed view taken from the section view of the front unit 200 presented in the FIG. 4A.
Figure 4C:
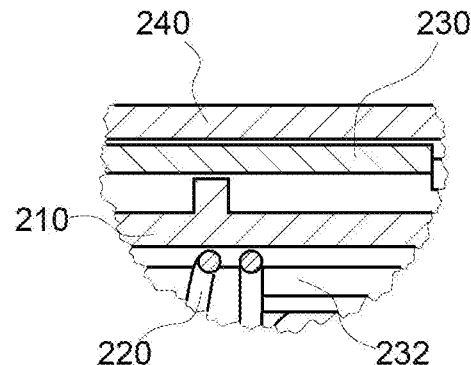
FIG. 4C is a detailed view of the front unit 200 taken from the FIG. 4A.
Figure 6:
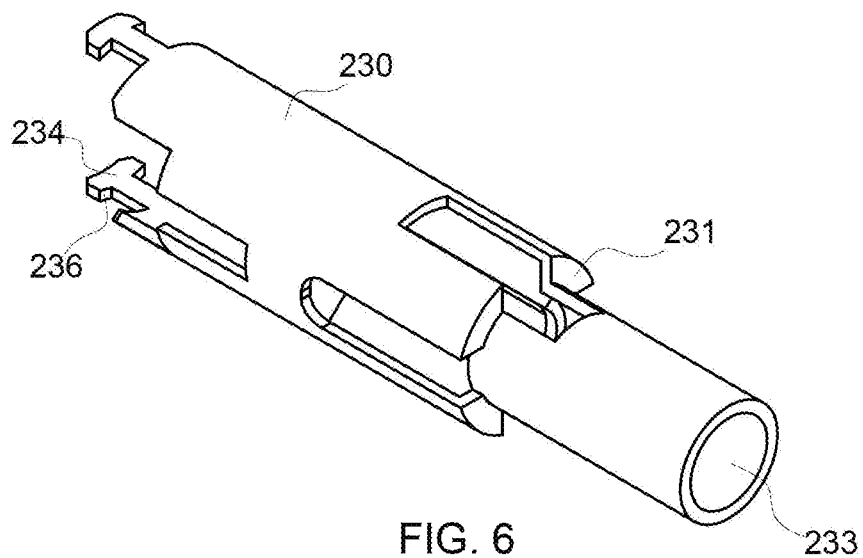
FIG. 6 is an isometric view of the activator 230.
Figure 6A:
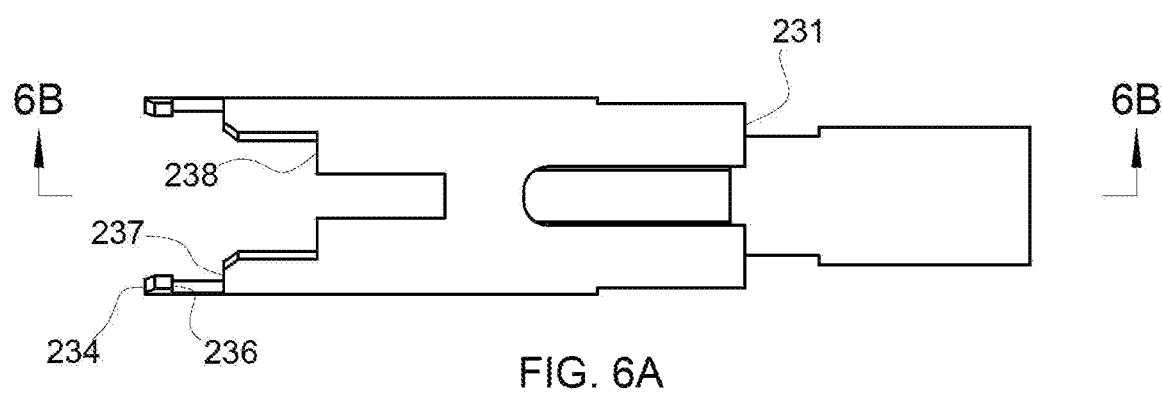
FIG. 6A is the side view of the activator 230 to present section line 6B-6B.
Figure 6B:
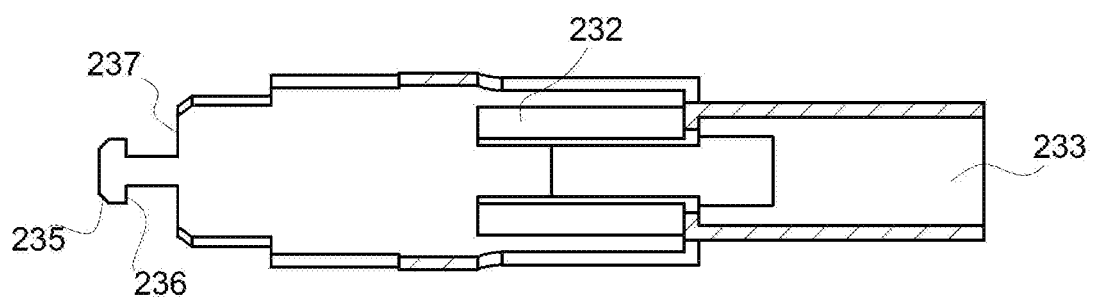
FIG. 6B is the cross-section view of the activator 230 taken along the section line 6B-6B on FIG. 6A.
Figure 7:
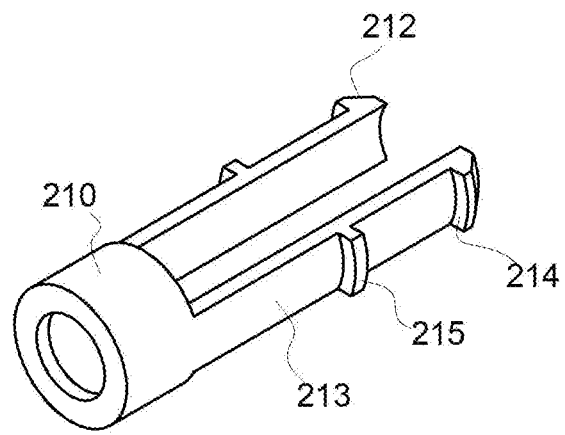
FIG. 7 is an isometric view of the syringe holder 210.
Figure 7A:
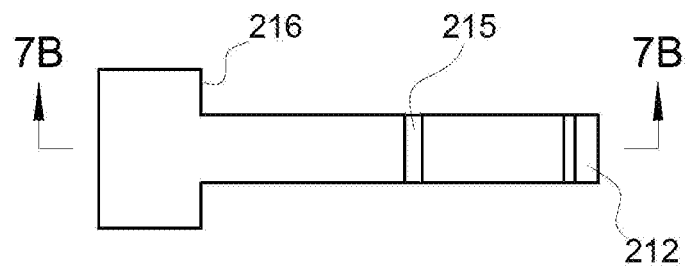
FIG. 7A is the side view of the syringe holder 210 to present the section line 7B-7B.
Figure 7B:
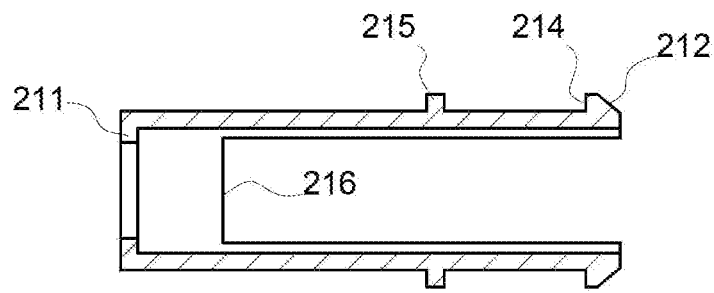
FIG. 7B is the cross-section view of the syringe holder 210 taken along the line 7B-7B on FIG. 7A.

After the ejection spring 220 is coaxially inserted into the activator 230 with the syringe holder 210 compressing the ejection spring 220 by the ribs 232 of the activator 230 illustrated in FIG. 6B and FIG. 4C against the rib 211 of the syringe holder 210 presented in FIG. 7B.

Figure 5:
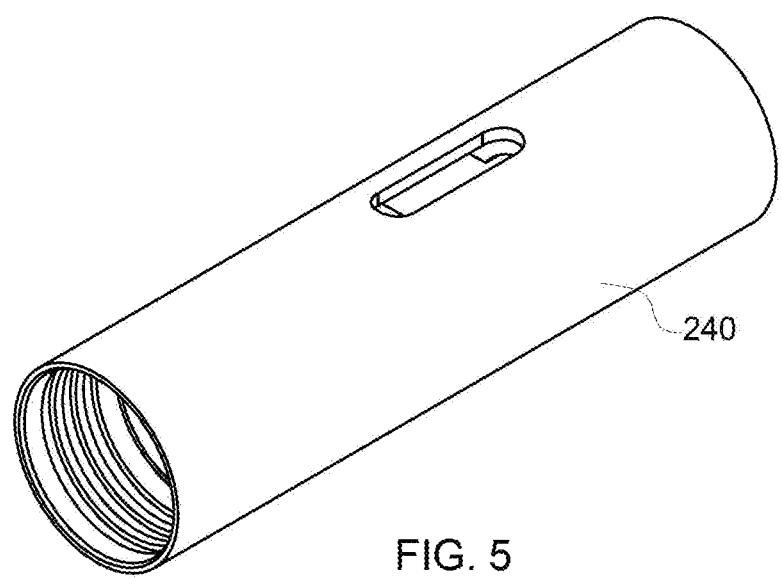
FIG. 5 is an isometric view of the front housing 240.
Figure 5A:
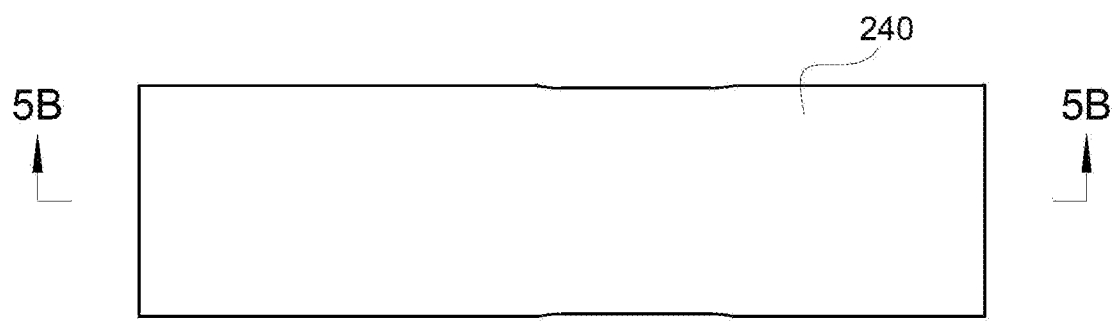
FIG. 5A is the side view of the front housing 240 to present the section line 5B-5B.
Figure 5B:
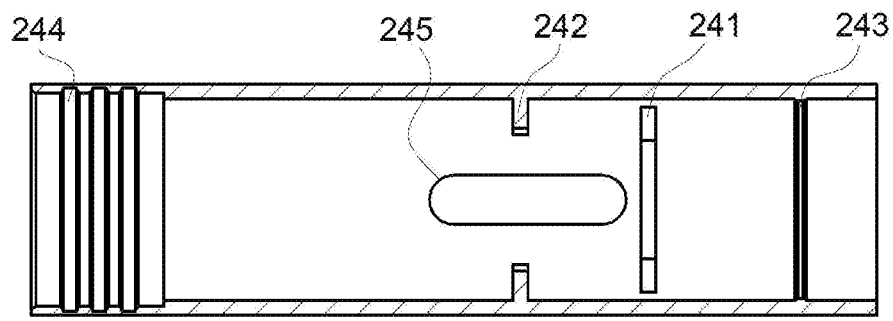
FIG. 5B is the cross-section view of the front housing 240 taken along the section line 5B-5B of the FIG. 5A.

Subsequent promotion of the syringe holder 210 inside the activator 230 leads to an interaction between the angled surface 212 of the syringe holder 210 shown in FIG. 7B against the ribs 242 of the front housing 240 presented in FIG. 5B.

For further advancement, the syringe holder 210 inside the activator requires a force to push the legs 213 of the syringe holder 210 illustrated in FIG. 7 to be bent inward and pushed until interlocked with the ribs 242 of the front housing 240 presented in FIG. 5B.

The surfaces 214 of the syringe holder 210 illustrated in FIG. 7B makes contact with the ribs 242 of the front housing 240, therefore, eliminate the possibility of the syringe holder 210 falling out as shown in FIG. 4A.

Thereby the preloaded spring 220 is in the locked position between the syringe holder 210 and the activator 230, thereby preventing the activator 230 from sliding out from the front housing 240.

Figure 8:
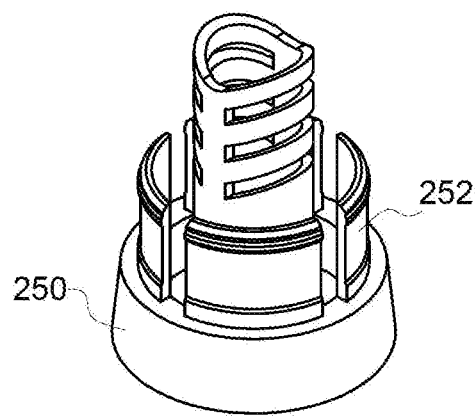
FIG. 8 is an isometric view of the cap 250.
Figure 8A:
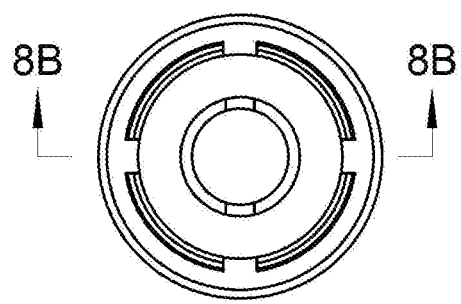
FIG. 8A is the side view of the cap 250 to present section line 8B-8B.
Figure 8B:
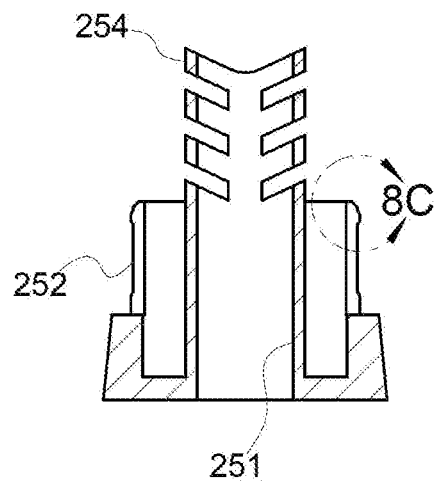
FIG. 8B is a cross-section view of the cap 250 taken along the line 8B-8B on FIG. 8A.
Figure 8C:
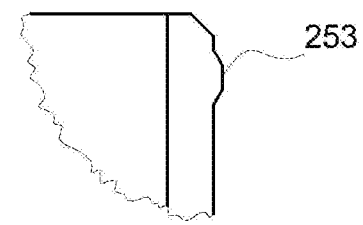
FIG. 8C is the detailed view taken from the section view of the cap 250 presented in the FIG. 8B.

The next step is mounting the cap 250 to another side of the front housing 240. The inner cylindrical portion 251 of the cap 250 shown in FIG. 8B slides into the cylindrical hole 233 of the activator 230 illustrated in FIG. 6B until the external legs 252 with the ribs 253 illustrated o FIG. 8C starts to interact with the rib 243 of the front housing 240 shown in FIG. 5B.

Further advancement of the cap 250, requires a force that can bend the legs 252 inwardly in order to pass over and snap behind the rib 243 of the front housing 240 demonstrated on FIG. 4B.

Therefore, the interaction between the front housing 240 and the cap 250 contributes to the retention of the parts together as illustrated in FIG. 4A.

At that moment the front unit is assembled.

The rear unit assembly 300 illustrated in FIGS. 9 and 9A which are the respective isometric pre-assembled view and the simplified exploded view accordingly.

The rear unit assembly 300 consists of the following components like the rear housing 370, the stopper 360 with the trigger 350 positioned coaxially to the rear housing 370 from one side respectively and the injection spring 310, the controller 320 with the syringe pusher 330 and the plunger 340 from another side.

Figure 10:
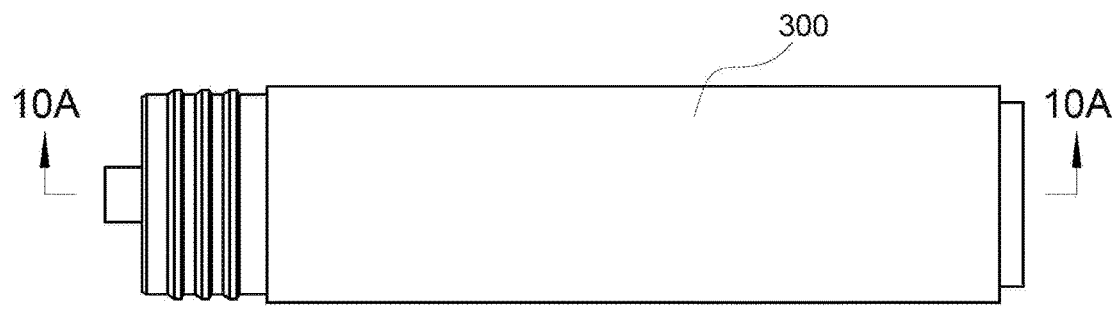
FIG. 10 is the side view of the rear unit 300 to present the section line 10A-10A.
Figure 10A:
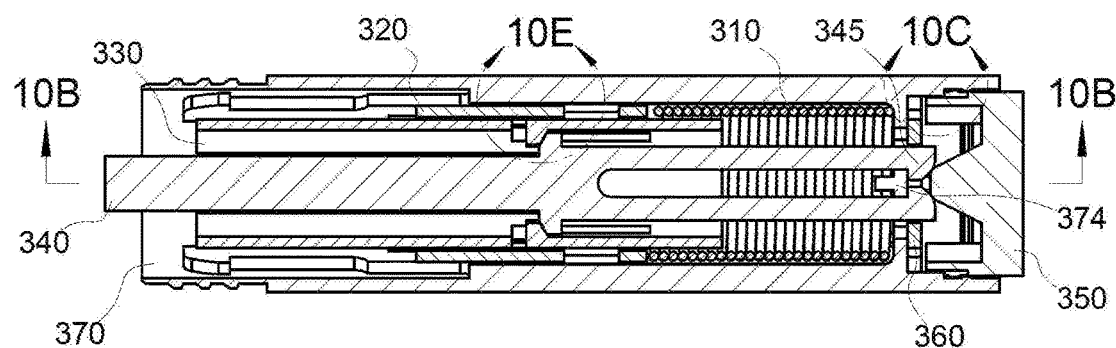
FIG. 10A is the cross-section view of the rear unit 300 taken along the section line 10A-10A on the FIG. 10.

Referring to FIGS. 10 and 10A illustrate the assembled rear unit 300 with the section line 10A-10A and side section view respectively for a better representation of the interaction and the location of the detailed parts among themselves in the assembled position.

Initially, install the injection spring 310 inside the rear housing 370. The injection spring 310 located coaxially between the internal ribs 371, 372 and 373 of the rear housing 370 indicated on FIG. 14B.

Whereupon, assemble the syringe pusher 330 with the plunger 340. To do this, insert the legs 341 of the plunger 340 illustrated on FIG. 13 into the syringe pusher 330 and locate the shoulders 342 of the plunger 340 inside the notch 331 presented in FIG. 12B.

Figure 12:
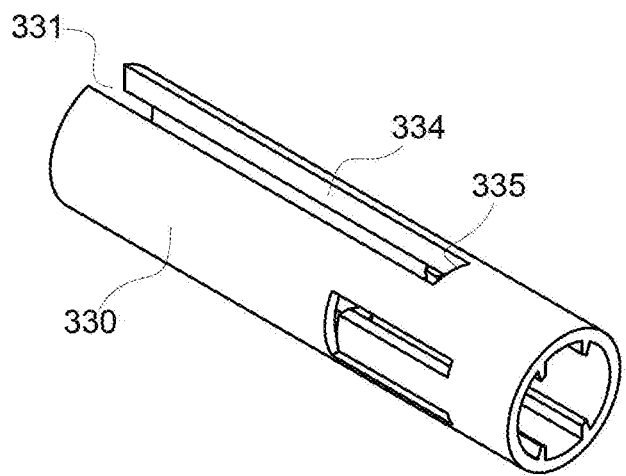
FIG. 12 is an isometric view of the syringe pusher 330.
Figure 12A:
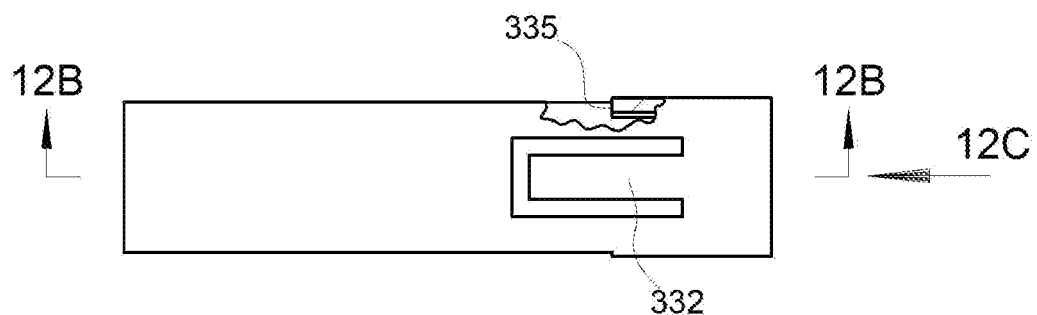
FIG. 12A is the side view of the syringe pusher 330 presented by section line 12B-12B and the break out view to show the hidden portion of the part, and the direction arrow for the side view 12C.
Figure 12B:
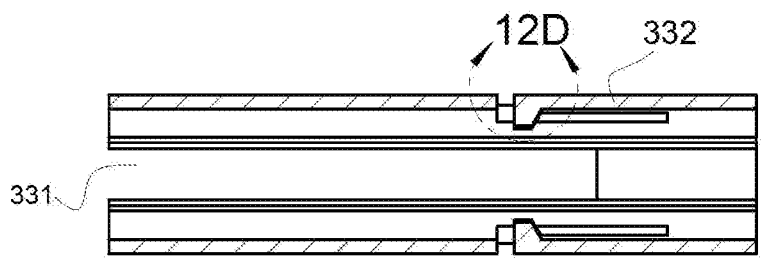
FIG. 12B is the cross-section view of the syringe pusher 330 taken along the section line 12B-12B on FIG. 12A.
Figure 12C:
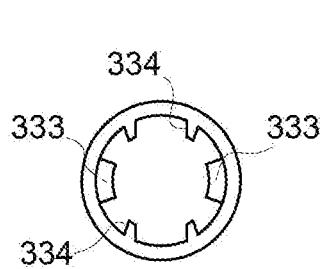
FIG. 12C is the side view of the syringe pusher 330 respectively to the view arrow 12C on the FIG. 12A.

The sidewalls 334 of the notches 331 presented in FIG. 12 and FIG. 12C interact with the shoulders 342 of the plunger 340 to prevent the rotation of the plunger 340 inside the syringe pusher 330.

Figure 12D:
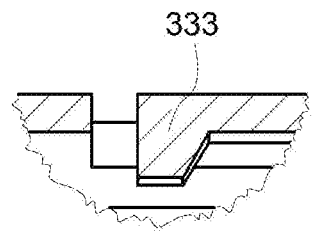
FIG. 12D is the detail view of the syringe pusher 330 taken from the FIG. 12B.

Further advancement of the plunger 340 inside the syringe pusher 330 requires preliminary outward bending of the legs 332 of the syringe pusher 330 illustrated in FIG. 12B in order to allow the ribs 343 of the plunger 340 to slip through the clamps 333 of the syringe pusher 330 shown in FIG. 12D.

Figure 10B:
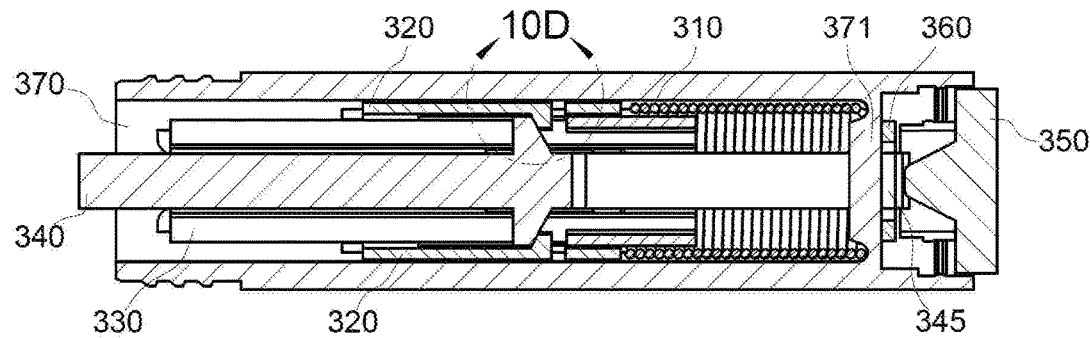
FIG. 10B is the cross-section view of the rear unit 300 taken along the line 10B-10B of the FIG. 10A.
Figures 10C, 10D, 10E:
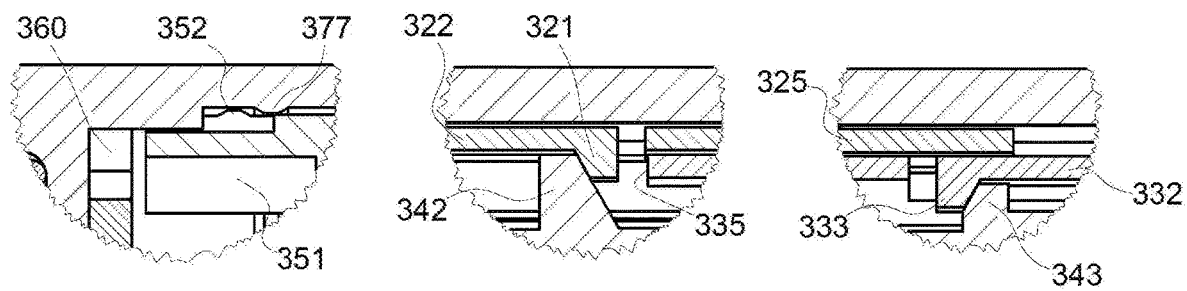
FIG. 10C is the detailed view of the rear unit 300 taken from the FIG. 10A.
FIG. 10D is a detailed view of the rear unit 300 taken from the FIG. 10B.
FIG. 10E is the detailed view of the rear unit 300 taken from the FIG. 10A.

When the ribs 343 of the plunger 340 passed the clamps 333 of the legs 332 of the syringe pusher 330 must be released and returned to the original position to snap over the ribs 343 of the plunger 340 and secure the plunger 340 inside the syringe pusher 330 as shown in FIG. 10E.

Upon then, the plunger 340 with the syringe pusher 330 must be inserted together into the controller 320.

Figure 11:
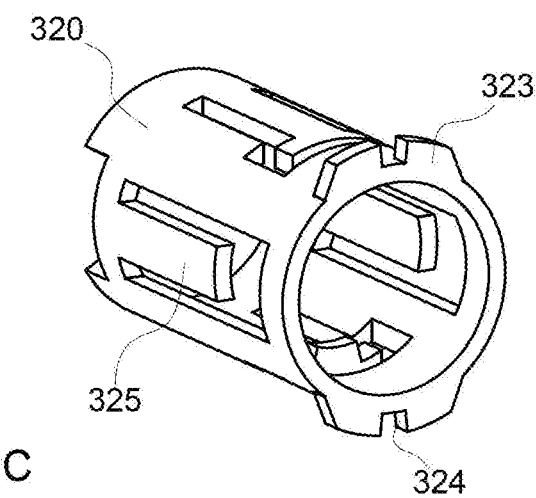
FIG. 11 is an isometric view of the controller 320.
Figure 11A:
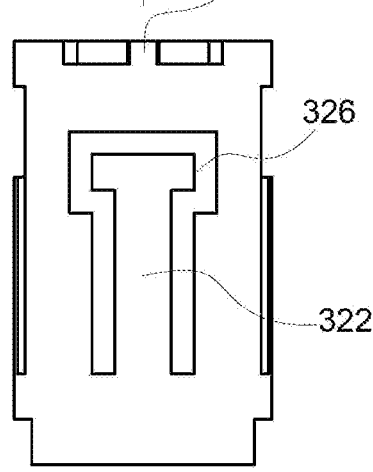
FIG. 11A is a side view of the controller 320 to present section line 11B-11B and the direction of the side view 11C.
Figure 11B:
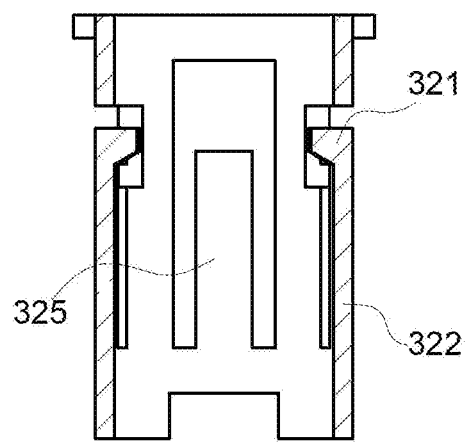
FIG. 11B is the cross-section view of the controller 320 taken along the section line 11B-11B of the FIG. 11A.
Figure 11C:
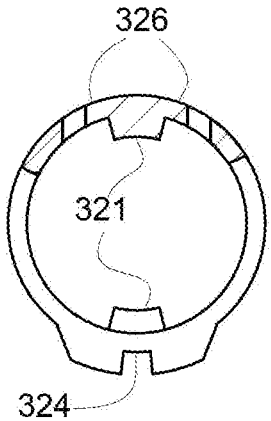
FIG. 11C is the side view of the controller 320 respectively to the arrow 11C on the FIG. 11A with the break out view to show a hidden portion of the controller 320.

After the syringe pusher 330 with the plunger 340 is inserted into the inside of the controller 320, an interaction occurs between the syringe pusher 330 and the clamps 321 of the controller 320 shown in FIG. 11C.

For further advancement, the syringe pusher 330 inside the controller 320 requires enough force in order to bend legs 322 with the clamps 321 of the controller 320 outward and slide on the external cylindrical surface of the syringe pusher 330. The legs 322 with the clamps 321 shown in FIG. 11B. Further movement of the syringe pusher 330 with the plunger 340 will cause the clamps 321 of the controller 320 to slip off from the external cylindrical surface of the syringe pusher 330 into the notches 331 as shown in FIG. 10D.

Thereby occurs the return of the legs 322 of the controller 320 to resting condition and blocking the clamps 321 of the controller 320 between the shoulders 342 of the plunger 340 and surface 335 of the syringe pusher 330.

Also, the sidewalls 334 of the syringe pusher 330 interacts with the clamps 321 of the controller 320 to prevent rotation relative to each other.

Therefore, the plunger 340, the syringe pusher 330 and the controller 320 interact with each other and cannot be disassembled without changing the shape of the parts.

Thereafter following the insertion of the assembled the plunger 340 with syringe pusher 330 and controller 320 into the rear housing 370.

For this purpose, insert the syringe pusher 330 into the injection spring 310 until the surface 323 of the controller 320 shown in FIG. 11 will interact with the injection spring 310 which was already pre-installed in the rear housing 370.

Further advancement of controller 320 leads to compression of the injection spring 310 inside the rear housing 370 between ribs 371, 372 and 373 which ensure the correct positioning of the injection spring 310.

When the controller 320 enters inside the rear housing 370, it is necessary that the ribs 371 of the rear housing 370 pass through the grooves 324 of the controller 320 presented in FIG. 11C to prevent rotation of the controller 320 with the syringe pusher 330 and plunger 340 inside the rear housing 370.

Figures 13, 13A, 13B:
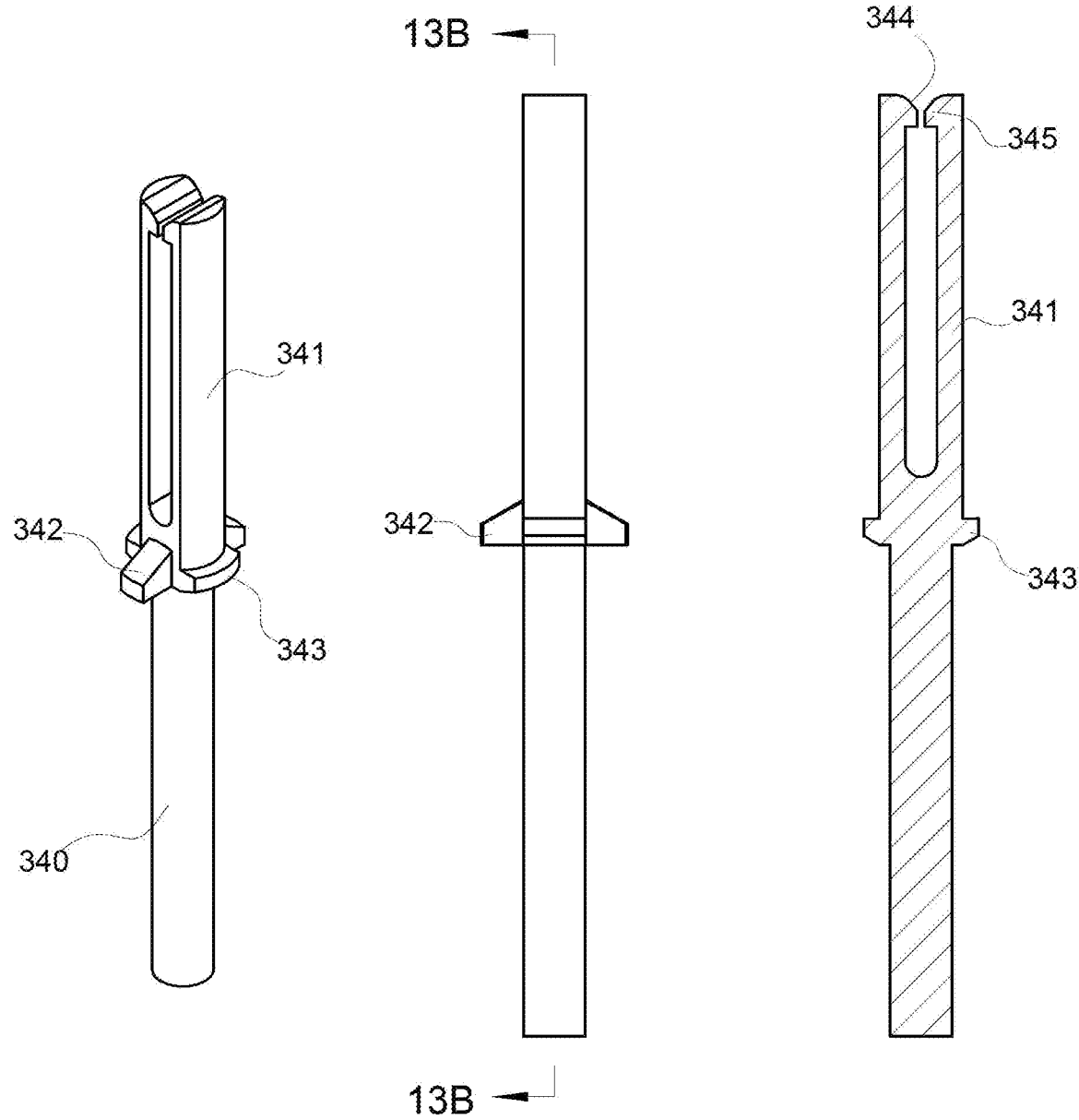
FIG. 13 is an isometric view of the plunger 340.
FIG. 13A is the side view of the plunger 340 to present section line 13B-13B.
FIG. 13B is the cross-section view of the plunger 340 taken along the section line 13B-13B on FIG. 13A.
Figure 14:
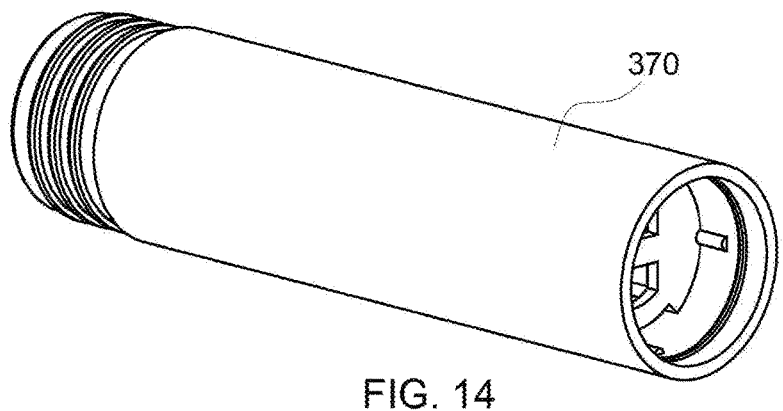
FIG. 14 is an isometric view of the rear housing 370.
Figure 14A:
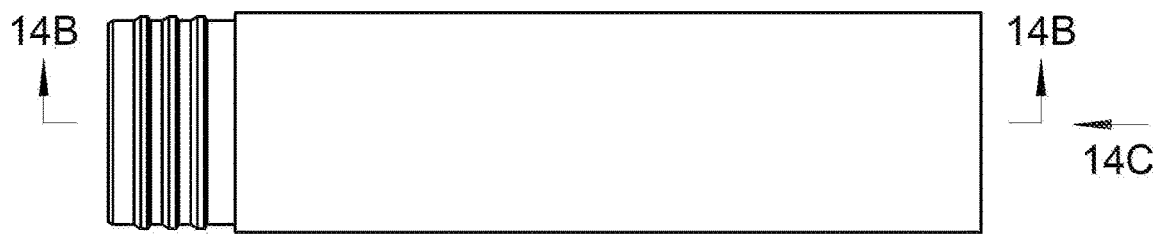
FIG. 14A is the side view of the rear housing 370 to present section line 14B-14B and direction arrow for the side view 14C.
Figure 14B:
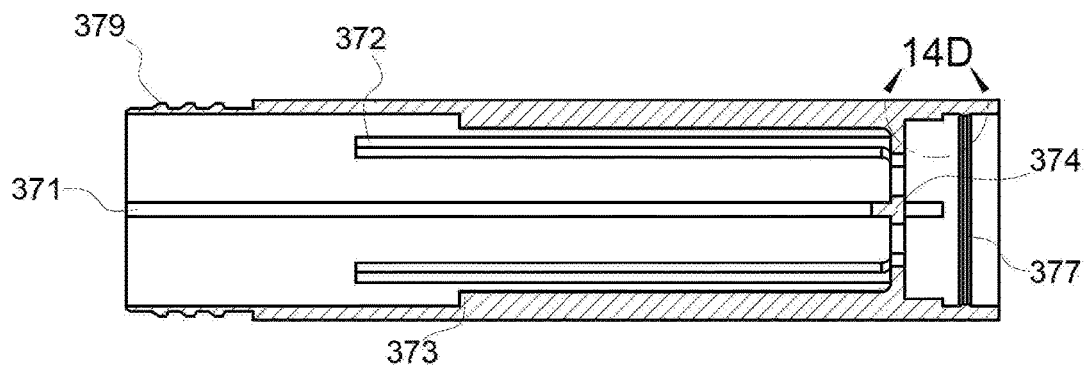
FIG. 14B is the cross-section view of the rear housing 370 taken along the section line 14B-14B on the FIG. 14A.
Figure 14C:
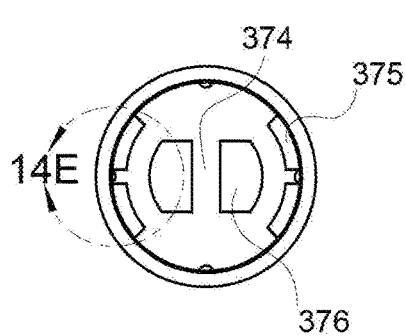
FIG. 14C is the side view of the rear housing 370 accordingly of the view arrow 14C on the FIG. 14A.
Figure 14D:
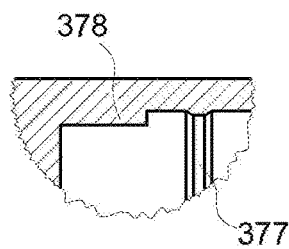
FIG. 14D is the detailed view of the rear housing 370 taken from the FIG. 14B.

Subsequent movement of the controller 320 with the syringe pusher 330 and the plunger 340 followed by compression the injection spring 310 inside the rear housing 370 leads to an interaction between the angled surface 344 of the plunger 340 shown in FIG. 13B against the bridge 374 of the rear housing 370 presented in FIG. 14C.

Thereby upon further movement, the legs 341 of the plunger 340 bends outwardly and locks 345 of the plunger 340 which crosses over the bridge 374 of the rear housing 370 and snap behind the bridge 374. Therefore, the plunger 340, the syringe pusher 330 and the controller 320 are locked at that position.

Likewise, the injection spring 310 remains in a compressed condition between the controller 320 and the rear housing 370, via plunger 340 as is presented in FIG. 10B. To avoid spontaneous release of the injection spring 310 with the subsequent displacement of the plunger 340 is necessary to prevent the legs 341 of the plunger to bend outward and does not allow the locks 345 to slide from the bridge 374 of the rear housing 370. For that purpose, it is necessary to install the stopper 360 from the other side of the rear housing 370.

Figure 14E:
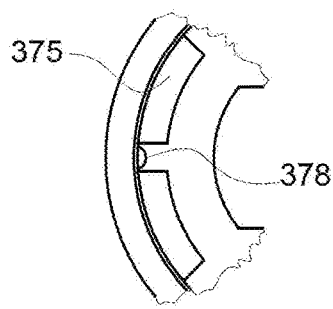
FIG. 14E is a detailed view of the rear housing 370 taken from the FIG. 14C.
Figure 15:
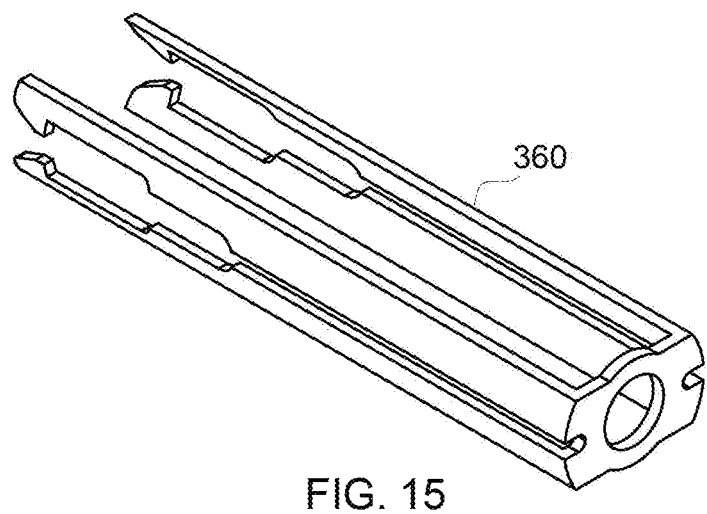
FIG. 15 is an isometric view of the stopper 360.
Figure 15A:
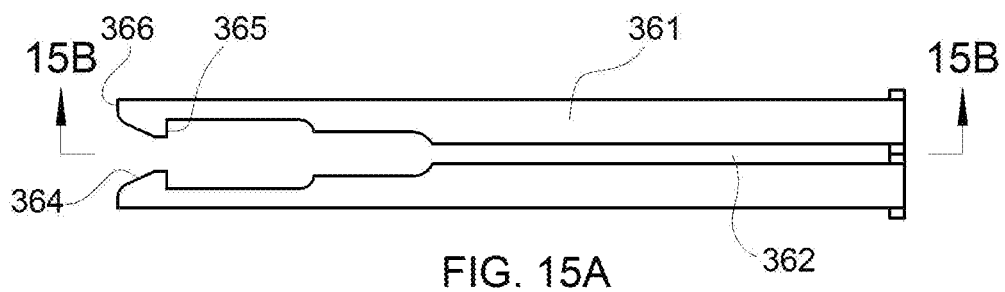
FIG. 15A is the side view of the stopper 360 to present the section line 15B-15B.

The legs 361 of the stopper 360 illustrated in FIG. 15A penetrate through the windows 375 presented in FIG. 14E.

The subsequent traveling of the legs 361 of the stopper 360 passes inside cylindrical surface of the rear housing 370 where the ribs 373 of the rear housing 370 settle between legs 361 in gaps 362 of the stopper 360 shown in FIG. 15A to prevent turning the stopper 360 inside the rear housing 370.

Figure 15B:
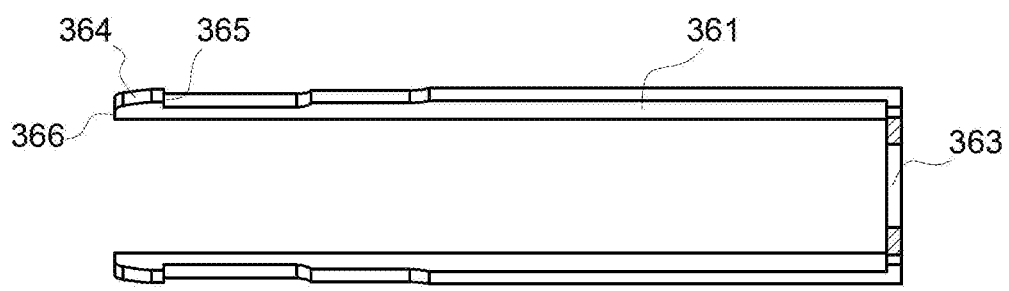
FIG. 15B is the cross-section view of the stopper 360 taken along the section line 15B-15B on the FIG. 15A.

With further progress, the stopper 360 into the rear housing 370, the locks 345 of the plunger 340 enters inside the hole 363 of the stopper 360 shown in FIG. 15B to ensure that the locks 345 will not slip off from the bridge 374 of the rear housing 370, which is demonstrated in FIG. 10A.

Figure 16:
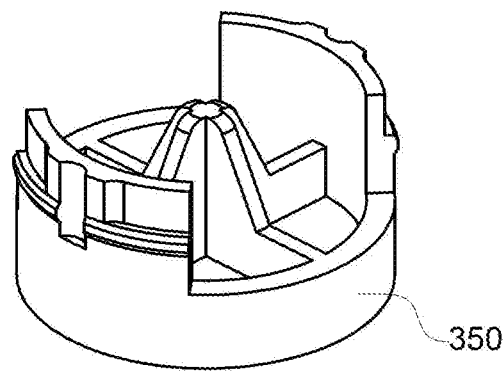
FIG. 16 is an isometric view of the trigger 350.
Figure 16A:
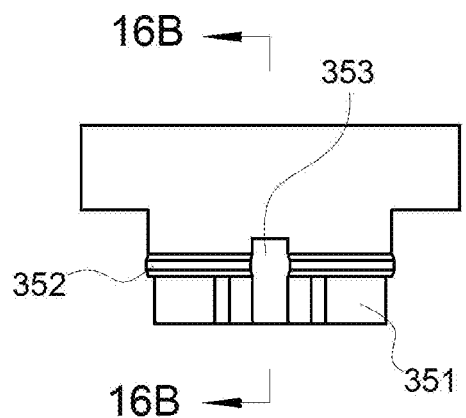
FIG. 16A is the side view of the trigger 350 to present section line 16B-16B.
Figure 16B:
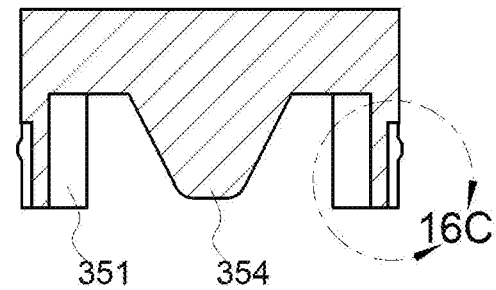
FIG. 16B is the cross-section view of the trigger 350 taken along the section line 16B-16B on the FIG. 16A.

To maintain the position of the stopper 360 at that condition, you must install the trigger button 350 shown in FIG. 16 into the rear housing 370. The trigger button 350 must be installed in such a way that its elongated parts 351 with the coaxial edges 352 presented in FIG. 16A is located in the same plane as the legs 361 of the stopper 360.

During installation, the trigger button 350 into the rear housing 370 the coaxial ribs 352 of the trigger button interact with the coaxial rib 377 of the rear housing 370 shown in FIG. 14B. To further advance the trigger button 350 into the rear housing 370, it is necessary to apply sufficient force to create an interaction between the rib 377 of the rear housing 370 and the coaxial ribs 352 of the trigger button in order to bend the elongated parts 351 of the trigger button 350 inwardly, crossing over and snapping behind the rib 377 of the rear housing, what present in FIGS. 10A and 10C.

Figure 16C:
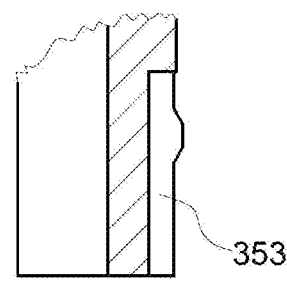
FIG. 16C is the detailed view of the trigger 350 taken from the FIG. 16B.

Also, the elongated parts 351 of the trigger button 350 have the cylindrical pockets 353 shown in FIG. 16C which coincide with the cylindrical protrusions 378 of the rear housing 370 presented in FIG. 14E, to prevent rotation the trigger button 350.

Therefore, the trigger button 350 located within the rear housing 370 thereby forbids change in position of the stopper 360, thereby, preventing the release of the locks 345 of the plunger 340, as shown in FIGS. 10A and 10B. At that moment the rear unit is assembled.

Figure 17:
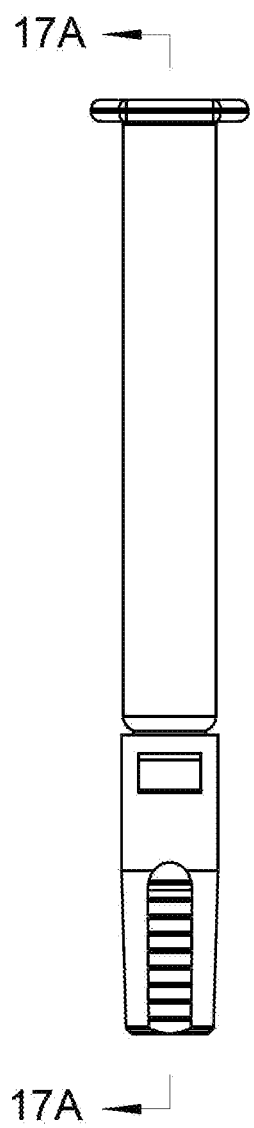
FIG. 17 is the side view of the syringe assembly 400 to present section line 17A-17A.
Figure 17A:
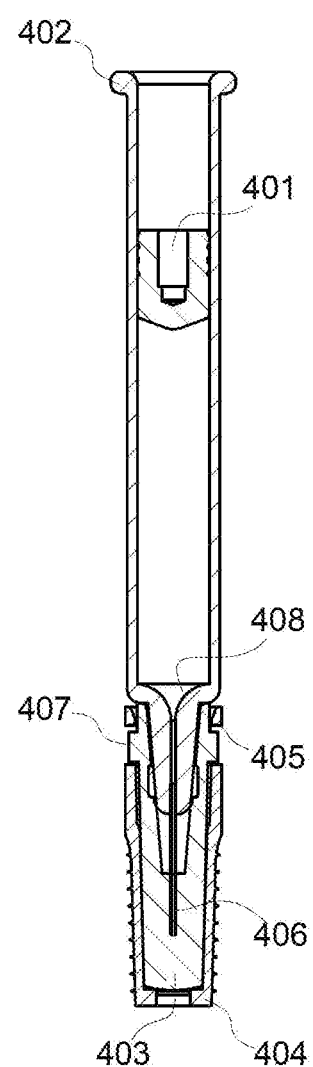
FIG. 17A is the cross-section view of the syringe assembly 400 taken along the section line 17A-17A of FIG. 17.
Figure 18A:
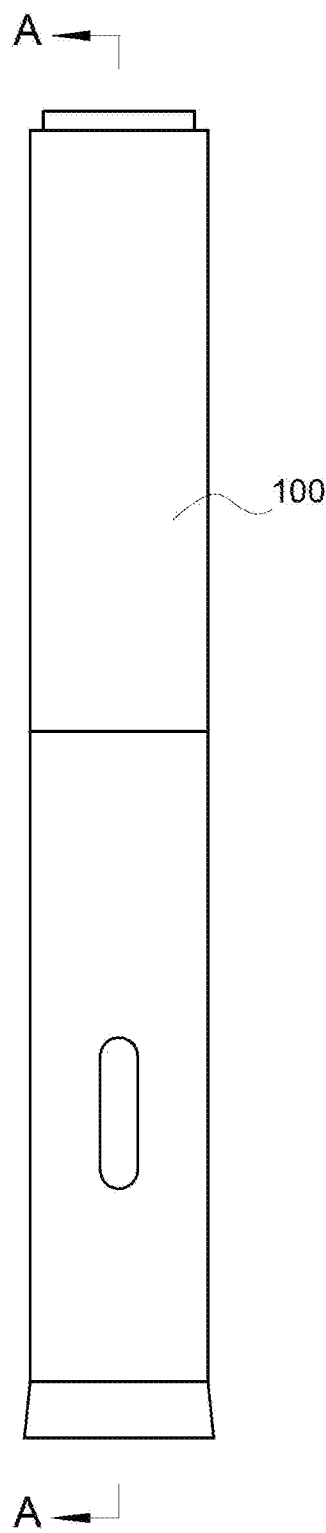
FIG. 18A is the window-side view of the auto-injector 100 to present section line A-A.
Figure 18B:
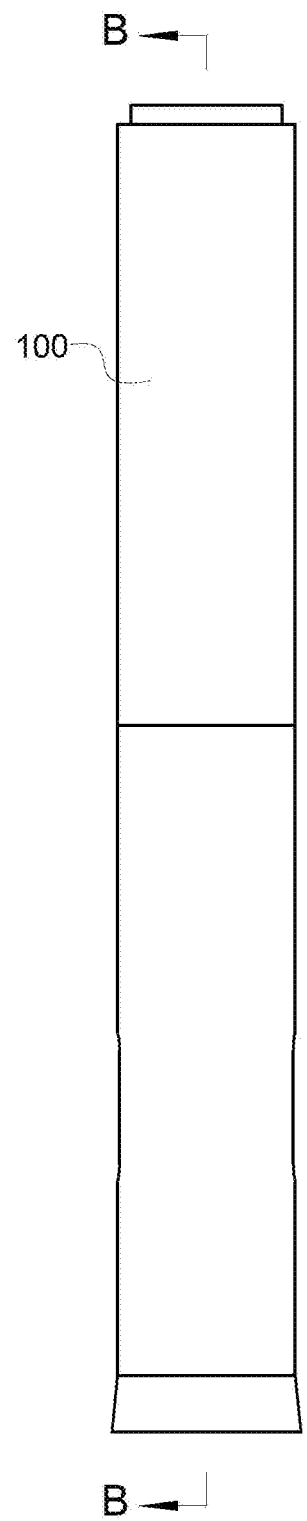
FIG. 18B is the 90 degree side view of the FIG. 18A to present section line B-B.

When the front and rear units are ready, they are delivered for final assembly with the syringe assembly 400 presented in FIGS. 17 and 17A which consists: the syringe 402, the needle 406, the piston 401 for sealing the medicine inside the syringe, and the sealer 403 is for sealing the needle 406 with rigid cover 404 to protect the needle from bending.

Initially, install the syringe assembly 400 into the front housing 200. For that, the syringe assembly 400 slides through the syringe holder 210 and ejection spring 220 until the cover 404 has to contact with the cap 250.

Further advancement, the cover 404 of the syringe assembly 400 must be placed into the inner cylindrical portion 251 of the cap 250. Further advancement of the cover 404, requires a force that can ensure the outward bend the inclined cylindrical ribs 254 to increase internal diameter of the inner cylindrical portion 251 for receiving the cover 404 and return the inclined ribs 254 to rest position to catch the cover 404 after it fully inserted into the cap 250 as illustrated in FIG. 19E.

Therefore, the cap 250 of the front unit 200 keeps the syringe assembly 400 inside the front unit 200, thereby preventing the syringe assembly 400 accidentally sliding out from the front unit 200.

Thereafter, assemble the front unit 200 with the rear unit 300 by aligning the T-locks 234 of the activator 230 shown in FIG. 6 which are situated inside the front unit 200 and the legs 361 of the stopper 360 located inside the rear unit 300.

When the rear housing 370 enters into the front housing 240, the plunger 340 located in the rear unit 300 advances inside the syringe 402 which is located in the front unit 200.

The subsequent movement of the rear unit 300 into the front unit 200 leads to an interaction between the legs 361 of the stopper with the T-lock 234 of the activator 230. To further advance the rear unit 300 into the front unit 200, it is necessary to apply sufficient force to create an interaction between the surfaces 235 of the T-locks 234 shown in FIG. 6B and surfaces 364 of the stopper 360 presented in FIG. 15A in order to bend the legs 361 of the stopper 360 outwardly, to pass over and snap behind the T-locks 234 of the activator 230.

Therefore, the legs 361 of the stopper 360 return to resting position, thereby the surfaces 365 of the stopper 360 have contact with surfaces 236 of the activator 230 and the surfaces 366 have contact with surfaces 237. Hence, the activator 230 and the stopper 360 are locked together and slides as one part inside the auto-injector 100.

Figure 19B:
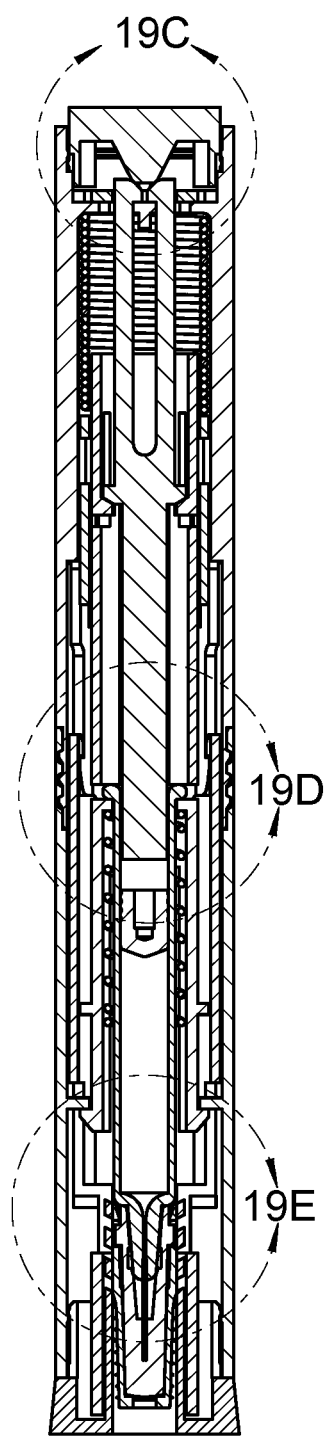
FIG. 19B is the cross-section view of the auto-injector 100 taken along the section line B-B on the FIG. 18B.
Figure 19C:
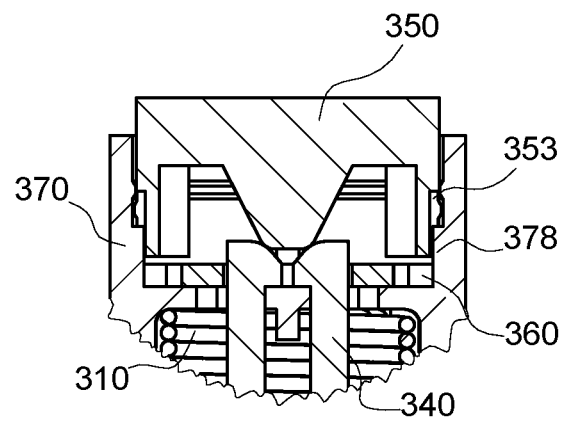
FIG. 19C is the detailed view of the auto-injector 100 taken from the FIG. 19B.
Figure 19D:
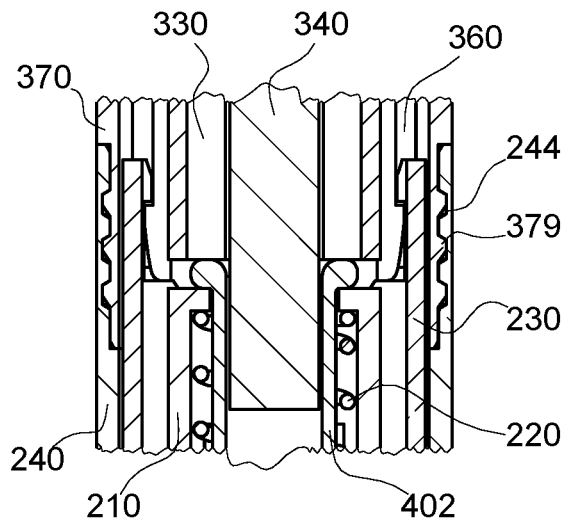
FIG. 19D is the detailed view of the auto-injector 100 taken from the FIG. 19B.
Figure 19E:
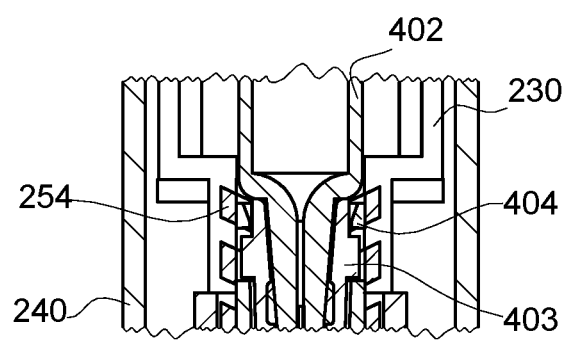
FIG. 19E is the detailed view of the auto-injector 100 taken from the FIG. 19B.

Thereafter, when the auto-injector 100 is assembled the cylindrical ribs 379 of the rear housing 370 snap with the grooves 244 of the front housing 240 to prevent separation the front unit 200 with the rear unit 300, what is presented in FIG. 19D.

Before releasing the auto-injector to the patients, it is necessary to unlock the stopper 360 by turning the trigger button 350 to a certain degree, until the pockets 353 of the trigger button 350 coincide with other cylindrical protrusions 378 of the rear housing 370 to prevent rotation the trigger button. After that, the stopper 360 no longer interferes with the trigger button 350 as shown in FIG. 20B. At this moment the auto-injector is ready to use by patients.

When a patient needs to inject medication, they should examine the auto-injector for medication through a window 245 of the front housing 240 presented in FIG. 5B.

During the inspection, it is impossible to activate the auto-injector spontaneously because the stopper 360 holds the locks 345 of the plunger 340 in the locked position on the bridge 374 as shown in FIG. 20B.

After inspection, the patient removes the cap 250 which has the incline ribs 254 engaged with the cover 404 of the syringe assembly 400. Also, the cover 404 joined with the needle sealer 403 by a notch 405 of the cover 404 and a ledge 407 of the needle sealer 403 respectively as illustrated in FIG. 20D.

Figure 20A:
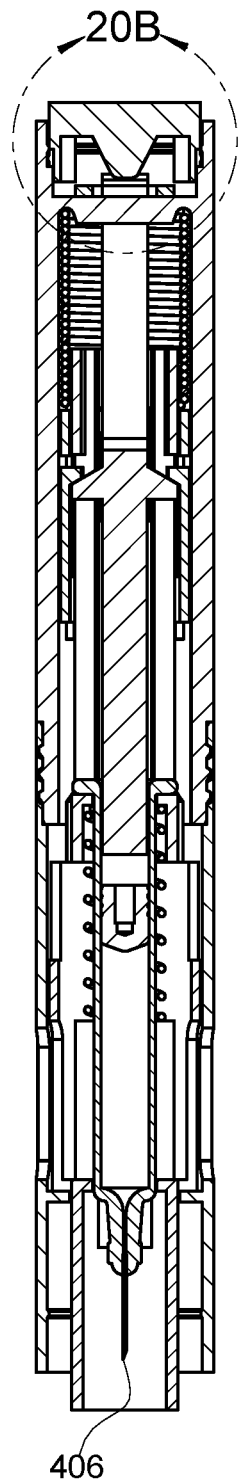
FIG. 20A is the cross-section view of the auto-injector 100 taken along the section line A-A on the FIG. 18A.
Figure 20B:
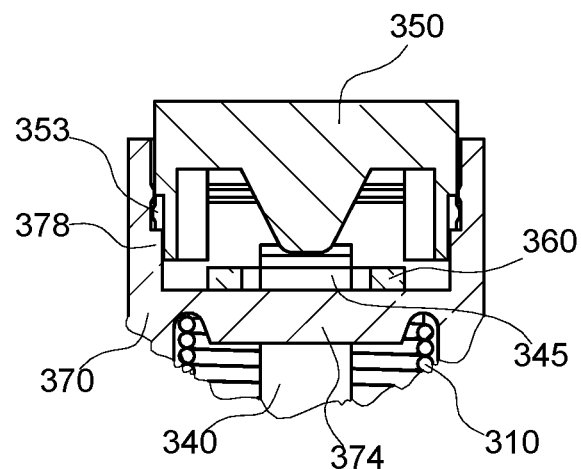
FIG. 20B is the detailed view of the auto-injector 100 taken from the FIG. 20A.
Figure 20C:
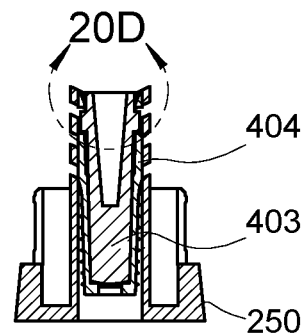
FIG. 20C is the cross-section view of the separated cap 250 from the auto-injector 100 taken along the line A-A on the FIG. 18A.
Figure 20D:
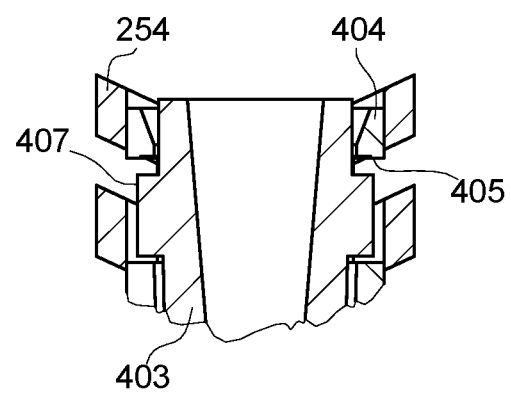
FIG. 20D is the detailed view taken from the FIG. 20C.

Therefore, the cap 250 separates and pulls off the cover 404 with the needle sealer 403 from the auto-injector 100 and unseals the needle 406 as shown in FIG. 20A. FIG. 20C illustrates the removed cap 250 with the cover 404 and the needle sealer 403.

Figure 21B:
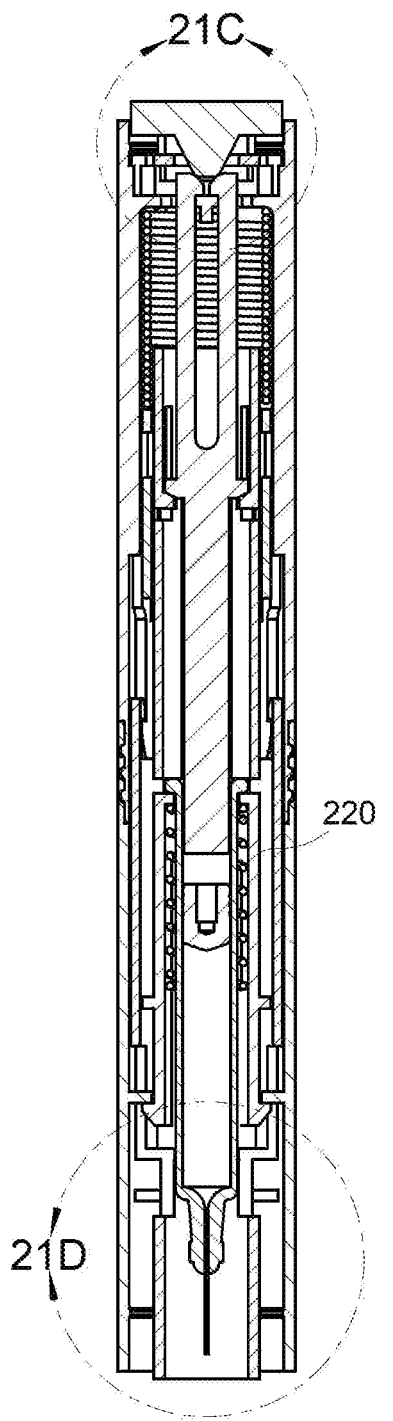
FIG. 21B is the cross-section view of the auto-injector 100 taken along the section line B-B on the FIG. 18B.
Figure 21C:
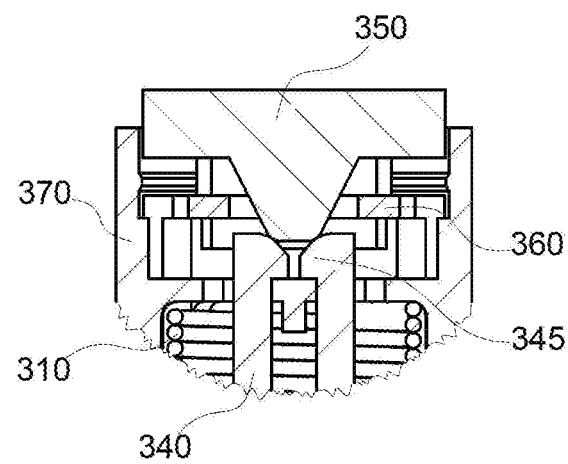
FIG. 21C is the detailed view of the auto-injector 100 taken from the FIG. 21B.
Figure 21D:
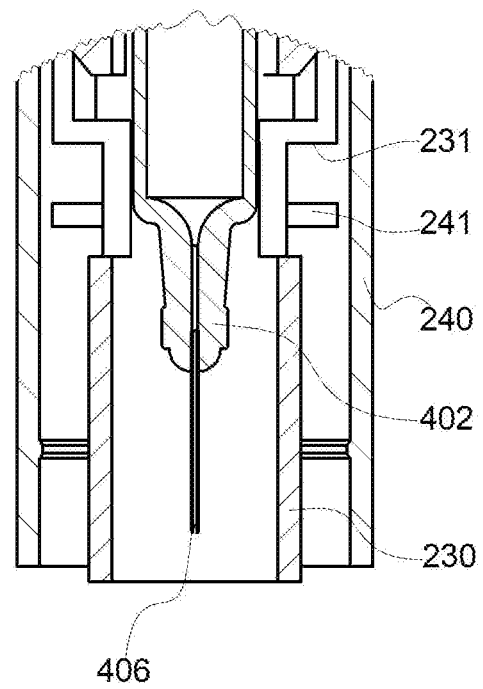
FIG. 21D is the detailed view of the auto-injector 100 taken from the FIG. 21B.

Then the patient shall press the auto-injector 100 to their body with enough force that displacement of the activator 230 inside the auto-injector 100 occurs which leads to the partial compression of the ejection spring 220 as illustrated in FIG. 21D.

As stated before, after the assembly of the front unit 200, with the rear unit 300, the activator 230, and the stopper 360 moves inside the auto-injector 100 to function as one part.

Consequently, the activator 230 dislocates the stopper 360 which leads to the release of the locks 345 of the plunger 340 as presented in FIG. 21C.

After that, the patient needs to press the trigger button 350 to activate the auto-injector 100 in order to ensure the injection of medicine.

Figure 22C:
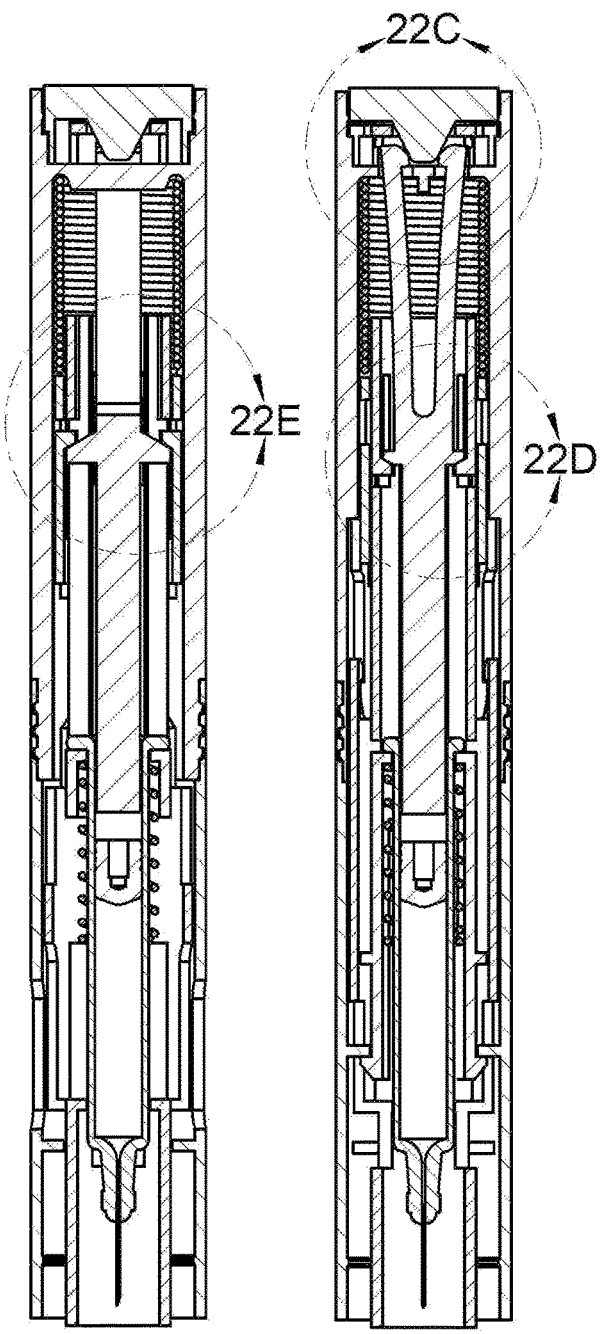
FIG. 22C is the detailed view of the auto-injector 100 taken from the FIG. 22B.
Figure 22C:
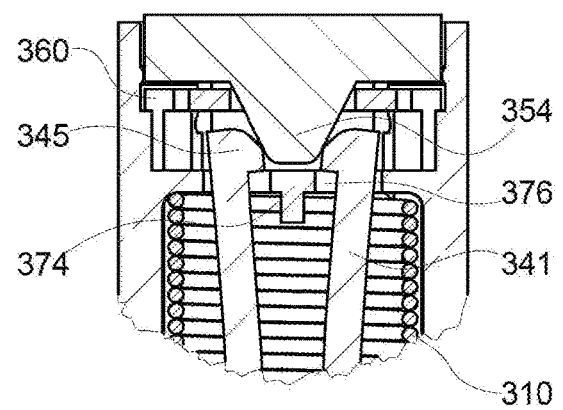

In the event when the patient presses the trigger button 350, a trapezoid portion 354 of the trigger button 350 comes in contact with the locks 345 of the plunger 340 and moves apart the locks 345 by bending the legs 341 of the plunger 340 as shown in FIG. 22C.

When the distance between locks 345 is bigger than the width of the bridge 374 of the rear housing 370, then the locks 345 shift into the windows 376 of the rear housing 370. See the FIG. 22C.

Figure 22D:
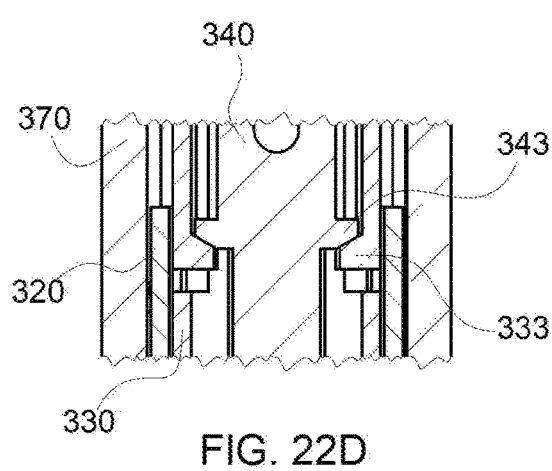
FIG. 22D is the detailed view of the auto-injector 100 taken from the FIG. 22B.
Figure 22E:
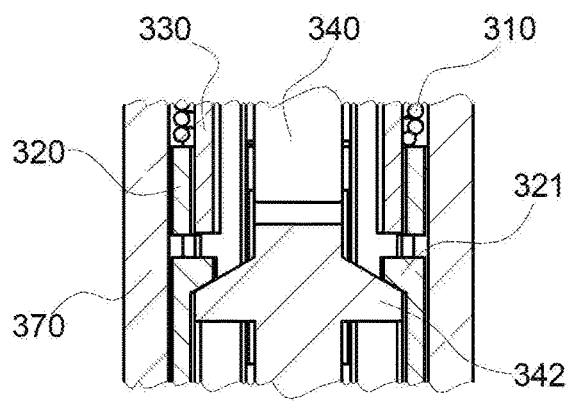
FIG. 22E is the detailed view of the auto-injector 100 taken from the FIG. 22A.

Occurring within the same time frame, the compressed injection spring 310 pushes the controller 320 which has the contact via the clamps 321 with the shoulders 342 of the plunger 340 as illustrated in FIG. 22E.

Therefore, the plunger 340 obtains freedom followed by displacement to the injection side and carrying the syringe pusher 330 which is connected by the clamps 333 with the ribs 343 of the plunger 340 as shown in FIG. 22D.

Thereupon, the controller 320, the plunger 340 and the syringe pusher 330 are released and now move as one.

The compressed injection spring 310 obtains a further extension and provides additional movement to the controller 320 towards the syringe side with the plunger 340 via the clamps 321 and the shoulder 342 accordingly as presented in FIG. 23D.

The plunger 340 also pushes the syringe pusher 330 via the ribs 343 and the clamps 333 accordingly as illustrated in FIG. 23C.

When the syringe pusher 330 travels to the injection side, it obtains contact with the syringe 402 which pushes the syringe 402 with the syringe holder 210 and compressing the ejection spring 220 as shown in FIG. 23E.

As was mentioned above the syringe 402 moves to the injection side whereby, the needle 406 moves out from the auto-injector 100 and penetrates the skin of the patient as presented in FIG. 23A and FIG. 23B.

The injection spring 310 extends more and continually pushes the controller 320 with the plunger 340 and the syringe pusher 330.

Also, the syringe pusher 330 shifts the syringe 402 with the syringe holder 210 and additionally compresses the ejection spring 220 until the lips 215 of the syringe holder 210 engage with the ribs 242 of the front housing 240 and stop the advancement of the syringe 402 as presented in FIG. 24E.

Simultaneously, the legs 325 of the controller 320 slip off from the ribs 373 of the rear housing 370 and are bent by the clamps 333 of the syringe pusher 330 which have a reaction from the ribs 343 of the plunger 340 which still continues move with the controller 320 by the injection spring 310 as shown in FIGS. 24C and 24D.

Further expansion of the injection spring 310 drive the controller 320 and the plunger 340 to the injection side of the Auto-Injector 100 and separate the syringe pusher 330 from the plunger 340 as illustrated in FIGS. 25C and 25D.

Contemporaneously, the plunger 340 travels inside fixed syringe 402 and got interaction with the piston 401 of the syringe assembly 400 as shown in FIG. 25E. Therefore, as stated above, we conclude that the device first inserts a needle into the patient's body and the medication is delivered later, eliminating the possibility of a spill.

Figure 26A:
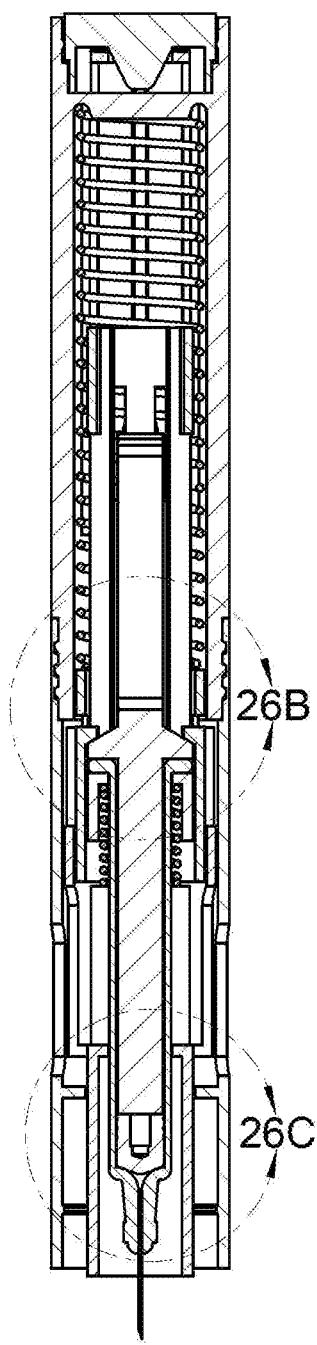
FIG. 26A is the cross-section view of the auto-injector 100 taken along the section line A-A on the FIG. 18A.
Figure 26B:
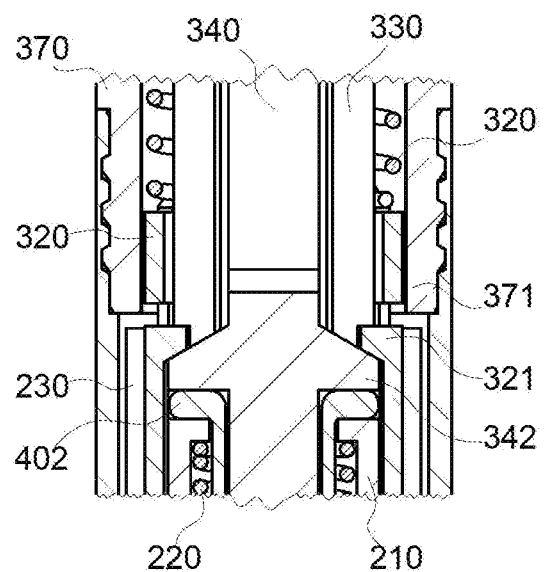
FIG. 26B is the detailed view of the auto-injector 100 taken from the FIG. 26A.

Subsequent expansion of the injection spring 310 shifts the controller 320 with the plunger 340 through interaction the clamps 321 with the shoulders 342 accordingly as presented in FIG. 26B.

The plunger 340 moves inside the stationary syringe 402 and pushes the piston 401 which creates pressure and pushes the medication through the needle 406 and delivering it into the patient's body.

When the plunger 340 moves inside the syringe 402, the controller 320 moves from the rear housing 370 into the activator 230.

Figure 26C:
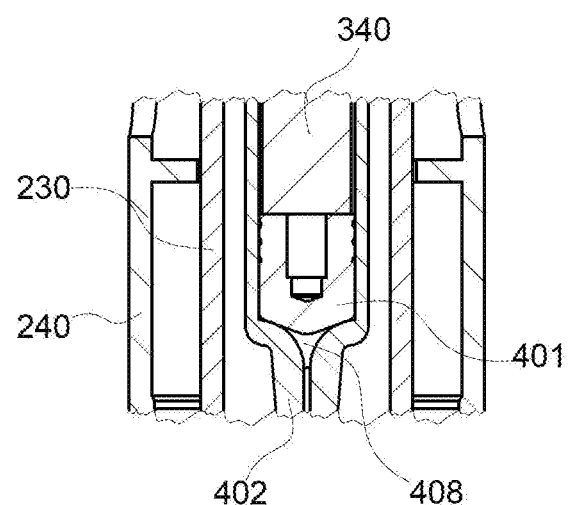
FIG. 26C is the detailed view of the auto-injector 100 taken from the FIG. 26A.

While the plunger 340 moves the piston 401 down to a stop surface 408 inside the syringe 402 and finishes the delivery of the medication entirely as shown in FIG. 26C, the clamps 321 of the controller 320 slide off from the ribs 371 of the rear housing 370 and come in contact with the activator 230 by via the protrusions 326 of the controller 320 in order the clamps 321 of the controller 320 have contact with the shoulders 342 of the plunger 340 as shown in FIGS. 26B and 27B.

Figure 28A:
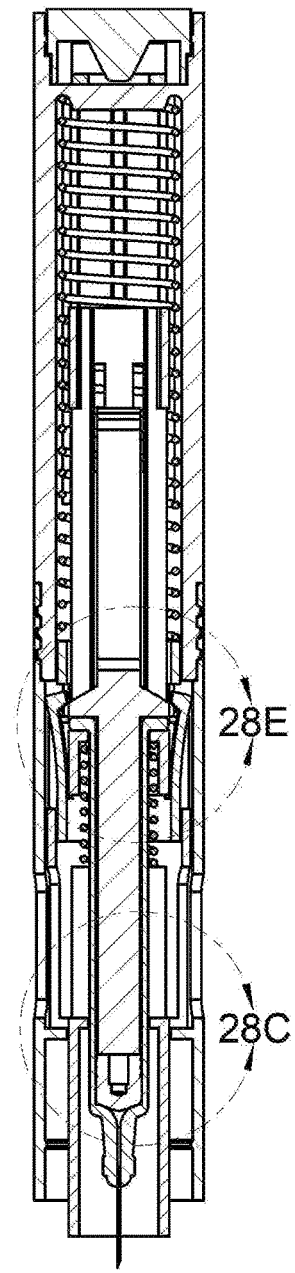
FIG. 28A is the cross-section view of the auto-injector 100 taken along the section line A-A on the FIG. 18A.
Figure 28B:
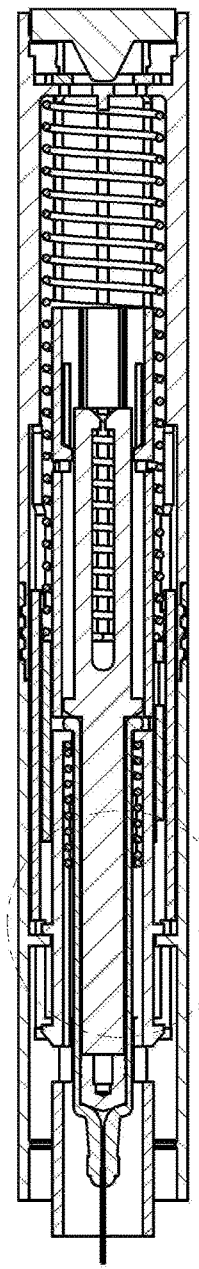
FIG. 28B is the cross-section view of the auto-injector 100 taken along the section line B-B on the FIG. 18B.
Figure 28C:
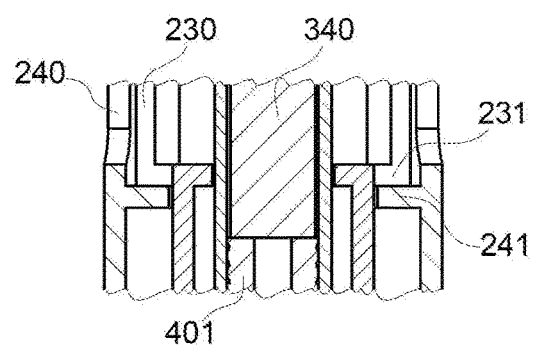
FIG. 28C is the detailed view of the auto-injector 100 taken from the FIG. 28A.
Figure 28D:
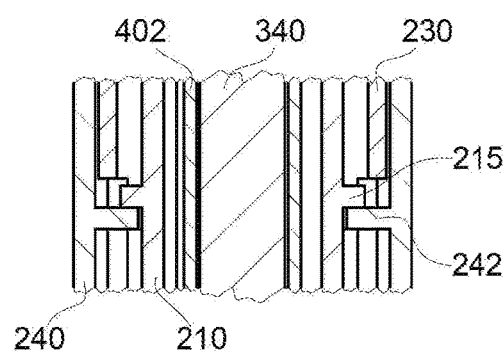
FIG. 28D is the detailed view of the auto-injector 100 taken from the FIG. 28B.

Therefore, the plunger 340 is still loaded by the injection spring 310 thus the controller 320 and keeps the syringe 402 in a fixed position due to the contact of the lips 215 of the syringe holder 210 with the ribs 242 of the front housing 240 as presented in FIG. 28D. Accordingly, the plunger 340 and controller 320 has a fixed position.

After all the medication has been administered to the patient, the patient moves the auto-injector 100 away from the body, as a result of which the activator 230 returns back towards the injection side by the pre-compressed ejection spring 220 until the stops 231 of the activator 230 adjoins with the ribs 241 of the front housing 240 as shown in FIG. 28C.

Figure 28E:
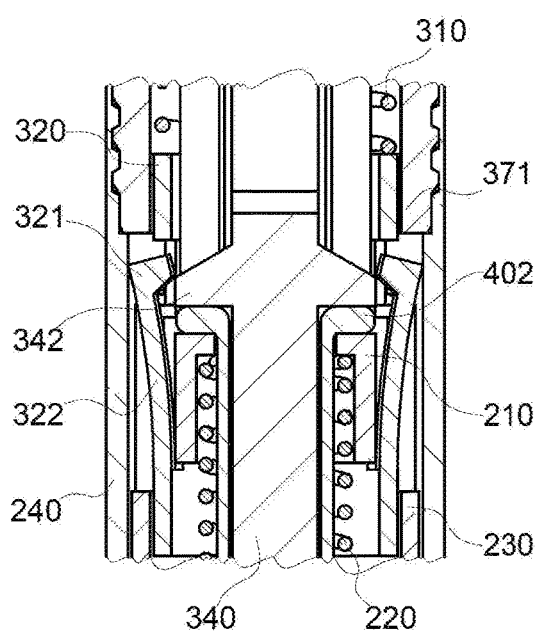
FIG. 28E is the detailed view of the auto-injector 100 taken from the FIG. 28A.
Figure 29A:
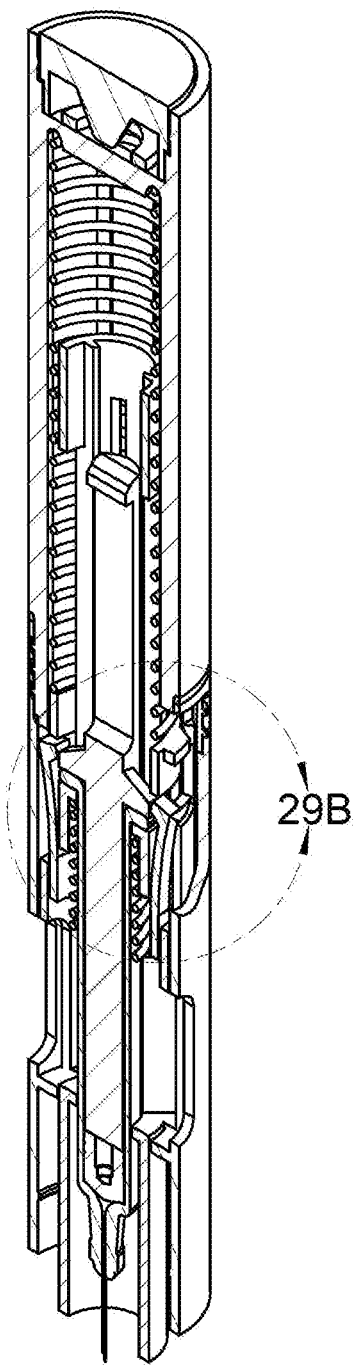
FIG. 29A is an isometric view of the FIG. 28A with the break out view to show the hidden portion of the part.
Figure 29B:
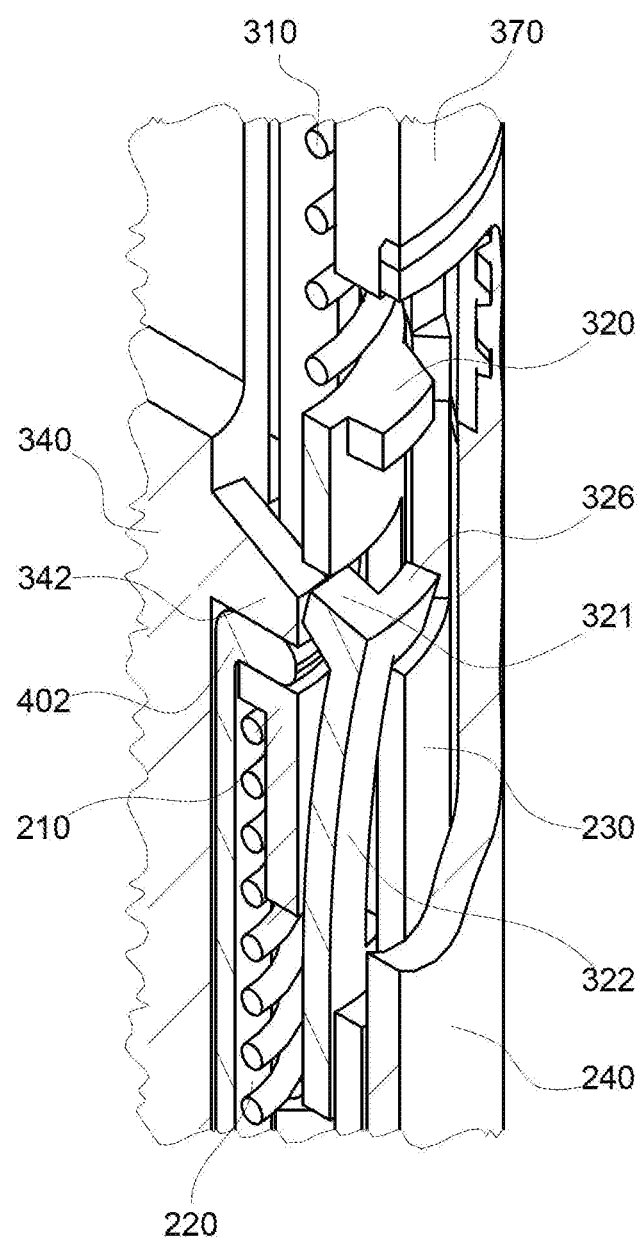
FIG. 29B is the detailed view of the auto-injector 100 taken from the FIG. 29A.

Since the activator has shifted relative to the controller, the protrusions 326 of the controller 320 are released by the activator 230 as shown in FIG. 28E and FIG. 29B.

This leads to an outward bending of the legs 322 of the controller 320 by the reaction between the clamps 321 of the controller 320 and the shoulders 342 of the pusher 340.

When the legs 322 are bent outward enough to allow clamps 321 of the controller 320 to slides off the shoulders 342 of the plunger 340 thereby breaking the connection between the controller 320 and the plunger 340.

Figure 30A:
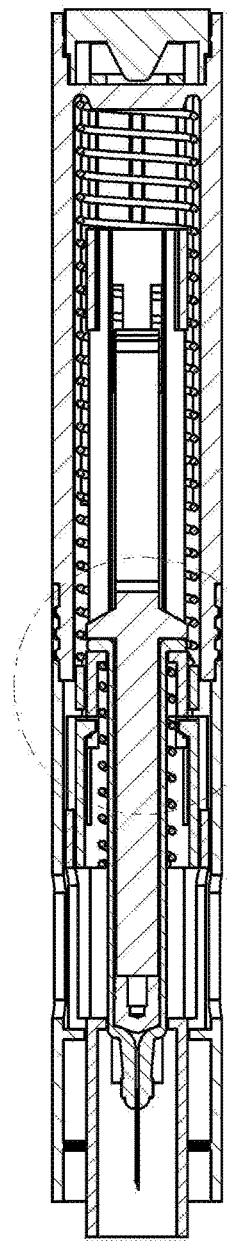
FIG. 30A is the cross-section view of the auto-injector 100 taken along the section line A-A on the FIG. 18A.
Figure 30B:
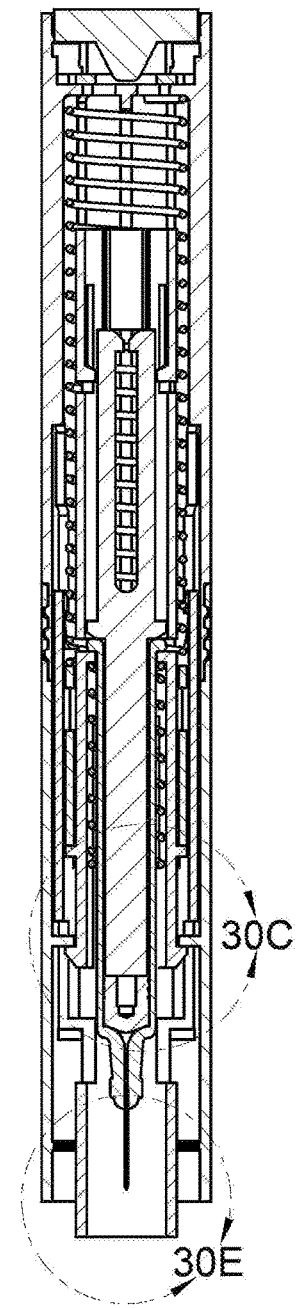
FIG. 30B is the cross-section view of the auto-injector 100 taken along the section line B-B on the FIG. 18B.
Figure 30C:
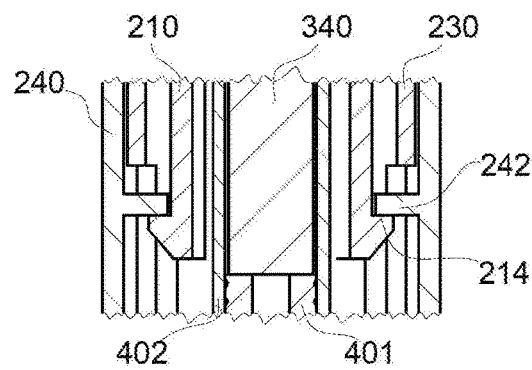
FIG. 30C is the detailed view of the auto-injector 100 taken from the FIG. 30B.

After the plunger 340 loses the related force from the injection spring 310 it moves with the syringe holder 210 with the syringe 402 into the second unit 300 by means of the ejector spring 220 until the surfaces 214 of the syringe holder 210 adjoins to the ribs 242 of the front housing 240 as illustrated in FIG. 30C.

Figure 30D:
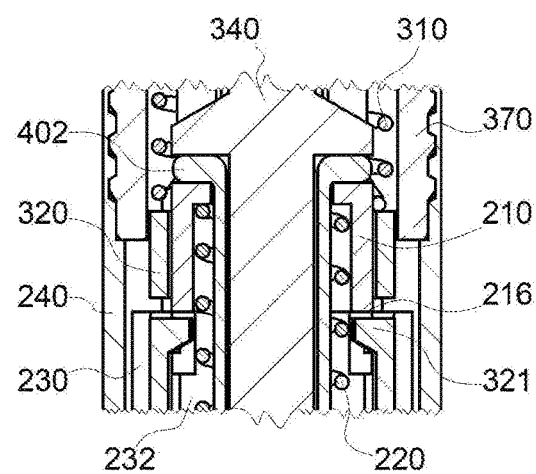
FIG. 30D is the detailed view of the auto-injector 100 taken from the FIG. 30A.

Then the plunger 340 with the syringe 402 and the syringe holder 210 moves into the second unit 300 allowing the clamps 321 of the controller 320 to shift inwardly between legs 213 of the syringe holder 210, snapping behind surface 216 as shown in FIG. 30D.

Furthermore, the controller 320 moves further by means of the injection spring 310 into the activator 230 until it links with the ribs 232 of the activator 230 keeping the activator 230 in an extended position as presented in FIG. 30D.

Moreover, when the controller 320 moves more to the injection side the protrusions 326 of the controller 320 regains contact with the activator 230.

Consequently, the clamps 321 of the controller 320 cannot move outward and will always have contact with the syringe holder 210 if the syringe holder 210 moves to the injection side of the Auto-Injector 100.

Figure 30E:
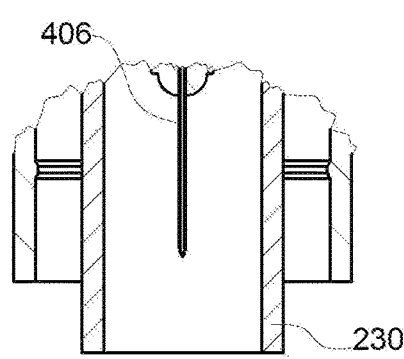
FIG. 30E is the detailed view of the auto-injector 100 taken from the FIG. 30B.

Therefore, the needle 406 of the syringe assembly 400 is not able to move close enough to the injection site as shown in FIG. 30E, because of the controller 320 located between the syringe holder 210 and the ribs 232 of the activator 230 to prevent accidental needle stick any person that may have contact with the auto-injector 100.

Through the window 245 of the front housing, the patient is visually able to see the piston 401 at the stop surface 408 of the syringe 402 which verifies that all medication was delivered.

I claim:

1. An auto-injector device, comprising:
   a front unit assembly connected with a rear unit assembly to protect a syringe assembly within, and administer a dose of a liquid medicament upon activation, wherein the syringe assembly comprises a syringe with a piston to seal the liquid medicament inside the syringe, a hollow needle, and a cover with a seal, the front unit assembly comprising:
   an elongated tubular front housing with a window through which a part of the syringe assembly is visible, and a locking member to connect with the rear unit assembly;
   an activator coaxially arranged inside the front housing, wherein the activator protrudes a distance outside the front housing to an injection site, and is adapted to connect with a stopper which slidably moves as one part with the activator after the front unit assembly is connected with the rear unit assembly;
   a syringe holder with the syringe slidably and coaxially arranged within the activator and cooperating with a plurality of transversal ribs of the front housing to control a traveling distance of the syringe to the injection site through an orifice of the activator to administer the dose of the liquid medicament, and to retract the syringe into a secure position after administering the dose of the liquid medicament;
   an ejection spring coaxially arranged between the activator and the syringe holder in a preloaded condition to keep the activator protruded from the front housing and the syringe holder with the syringe assembly away from the injection site in the secure position; and
   a cap coaxially coupled with the front housing to protect the activator and receive the cover of the syringe assembly after installing the syringe assembly into the front unit assembly;
   the rear unit assembly comprising:
   an elongated tubular rear housing with a plurality of longitudinal internal ribs interacting with a controller, and a locking member to connect with the front unit assembly;
   a syringe pusher slidably and coaxially arranged within the controller and adapted to receive a driving force from a plunger via the controller to move the syringe to the injection site;
   the plunger, being coaxially arranged within the syringe pusher, which connects to a bridge of the rear housing by inward cams of flexible legs of the plunger to keep an injection spring by the controller in a compressed condition, and is adapted to receive the driving force from the controller to move the syringe pusher and the piston of the syringe to the injection site;
   the injection spring, being coaxially arranged within the plurality of longitudinal internal ribs of the rear housing and maintained in the compressed condition by the controller via the plunger interacting with the rear housing, which generates the driving force;
   the controller, being slidably and coaxially arranged inside the rear housing via interaction with the plurality of longitudinal internal ribs of the rear housing, which distributes the driving force of the injection spring between the plunger and the syringe pusher to move the syringe to the injection site, and after administering the dose of liquid medicament, cooperates with the activator to release the syringe holder and the syringe to return into the secure position;
   the stopper, being coaxially arranged within the rear housing between the plurality of longitudinal internal ribs of the rear housing, which secures a connection of the plunger with the rear housing, and is adapted to connect with the activator to slidably move as one part after the front unit assembly connects with the rear unit assembly; and
   a trigger slidably and coaxially coupled within the rear housing in a manner to protrude from the rear housing, the trigger including legs that latch within the rear housing to prevent separation with the rear housing, and a trapezoid member which interacts with inward cams of the plunger to release the legs of the plunger.

2. The auto-injector device of claim 1, wherein the cap comprises an inner cylindrical member with inclined flexible annular inwardly directed ribs adapted to interact with the cover of the syringe assembly.

3. The auto-injector device of claim 2, wherein said ribs of the cap adapt to interact with the cover of the syringe assembly by bending outwardly during insertion thus providing a circumferential gap between the cover and ribs of the cap, and increase engagement between the ribs of the cap with the cover when pulling the cap.

4. The auto-injector device of claim 1, wherein the controller comprises inwardly directed cams arranged at flexible legs supported by the longitudinal internal ribs of the rear housing in order to prevent from bending outward and slipping past from the shoulders of the plunger.

5. The auto-injector device of claim 4, wherein said after administering the dose of the liquid medicament, the controller cooperates with the activator means the inwardly directed cams arranged at flexible legs of the controller slide from the longitudinal internal ribs of the rear housing into the activator to receive support for the inwardly directed cams of the controller to prevent bending outward and slipping past from a shoulder of the plunger.

6. The auto-injector device of claim 4, wherein said releasing the syringe holder and the syringe to return into the secure position means the activator moved to the injection site releases the inwardly directed cams arranged at flexible legs of the controller which bend outwardly and lose the connection with a shoulder of the plunger to let the syringe holder, the syringe and the plunger move into the secure position by the ejection spring.

7. The auto-injector device of claim 4, wherein said lock in a secure position means the injection spring pushes the controller to the injection site to let the inwardly directed cams arranged at flexible legs of the controller slide within the activator and reobtain support from the activator to prevent the flexible legs of the controller from bending outward, locking the syringe holder in the secure position.

8. The auto-injector device of claim 1, wherein the syringe pusher comprises inwardly directed cams arranged at flexible legs supported by the flexible legs of the controller which cooperate with the longitudinal internal ribs of the rear housing in order to prevent from bend outward and slip past from a plurality of ribs of the plunger.

9. The auto-injector device of claim 1, wherein the plunger is adapted to receive the driving force from the controller via shoulders of the plunger and transfer the driving force via a plurality of ribs of the plunger to the syringe pusher and the piston of the syringe to the injection site.

10. The auto-injector device according to claim 1, wherein said secure connection of the plunger with the rear housing means the stopper with inward cams of the plunger to prevent separation with the rear housing.

11. The auto-injector device of claim 1, wherein the legs of the trigger comprise pockets which correlate with certain protrusions on the rear housing to position the legs of the trigger against the stopper to prevent a trigger motion to the inward cams of the plunger.

12. The auto-injector device of claim 11, wherein said correlation with the certain protrusions on the rear housing means the trigger is able to coaxially rotate inside the rear housing to snap with other protrusions to avoid interference between the legs of the trigger and the stopper, and allows stopper slides to unlock the inward cams of the plunger.

\* \* \* \* \*